(12) United States Patent
Markus et al.

(10) Patent No.: US 10,395,326 B2
(45) Date of Patent: Aug. 27, 2019

(54) COLLECTIONS OF LINKED DATABASES

(75) Inventors: Michael J. Markus, Plymouth Meeting, PA (US); Heather A. McGuire, Plymouth Meeting, PA (US); Brian N. Smith, Plymouth Meeting, PA (US); Peter M. Kionga-Kamau, Charlottesville, VA (US)

(73) Assignee: 3DEGREES LLC, Plano, TX (US)

( * ) Notice: Subject to any disclaimer, the term of this patent is extended or adjusted under 35 U.S.C. 154(b) by 1000 days.

(21) Appl. No.: 11/686,421

(22) Filed: Mar. 15, 2007

(65) Prior Publication Data

US 2008/0228746 A1  Sep. 18, 2008

Related U.S. Application Data

(63) Continuation of application No. PCT/US2005/041349, filed on Nov. 15, 2005.

(51) Int. Cl.
*G06F 16/00* (2019.01)
*G06Q 50/22* (2018.01)
(Continued)

(52) U.S. Cl.
CPC .......... *G06Q 50/22* (2013.01); *G06F 16/951* (2019.01); *G06F 16/9536* (2019.01); *G06Q 10/10* (2013.01); *G16H 80/00* (2018.01)

(58) Field of Classification Search
CPC ........ G06Q 50/01; G06Q 50/22; G06Q 10/10; G06F 17/30699; G06F 17/30761; G06F 16/951; G06F 16/9536; G16H 80/00
See application file for complete search history.

(56) References Cited

U.S. PATENT DOCUMENTS

| | | |
|---|---|---|
| 3,509,930 A | 5/1970 | Martain |
| 4,640,329 A | 2/1987 | Nakasaki et al. |
| | (Continued) | |

FOREIGN PATENT DOCUMENTS

| | | |
|---|---|---|
| EP | 1288795 | 3/2003 |
| EP | 1338966 | 8/2003 |
| | (Continued) | |

OTHER PUBLICATIONS

"A Model of Network Capitalism: Basic Ideas and Post-Soviet Evidence", Journal of Economic Issues, Mar. 2004, vol. 38, No. 1, pp. 85-111.

(Continued)

*Primary Examiner* — Alexander Khong
(74) *Attorney, Agent, or Firm* — Fay Sharpe LLP

(57) ABSTRACT

In accordance with the teachings described herein, systems and methods are provided for conducting a search of a network for information related to a topic specified by a search initiator. A query may be generated that includes search information and a first-degree contact. The first-degree contact may be an electronic record that represents a member of the social network, and the search information may identify the topic. One or more electronic records that each represent a social-network member may be searched using the query to identify one or more social-network members that are identified in connection with the topic and who are directly or indirectly associated with the first-degree contact.

17 Claims, 17 Drawing Sheets

(51) Int. Cl.
  *G06F 16/9536* (2019.01)
  *G06Q 10/10* (2012.01)
  *G16H 80/00* (2018.01)
  *G06F 16/951* (2019.01)

(56) References Cited

U.S. PATENT DOCUMENTS

| | | | |
|---|---|---|---|
| 4,790,366 A | | 12/1988 | Kadota |
| 5,309,355 A | | 5/1994 | Lockwood |
| 5,576,951 A | | 11/1996 | Lockwood |
| 5,768,552 A | | 6/1998 | Jacoby |
| 5,911,687 A | | 6/1999 | Sato et al. |
| 6,016,475 A | | 1/2000 | Miller et al. |
| 6,103,275 A | | 8/2000 | Seitz et al. |
| 6,108,493 A | | 8/2000 | Miller et al. |
| 6,112,181 A | * | 8/2000 | Shear ................. G06F 21/10 705/7.29 |
| 6,151,581 A | | 11/2000 | Kraftson et al. |
| 6,175,831 B1 | * | 1/2001 | Weinreich et al. ............. 707/10 |
| 6,223,165 B1 | | 4/2001 | Lauffer |
| 6,269,369 B1 | | 7/2001 | Robertson |
| 6,302,844 B1 | | 10/2001 | Walker et al. |
| 6,321,228 B1 | * | 11/2001 | Crandall et al. |
| 6,327,590 B1 | * | 12/2001 | Chidlovskii et al. ............ 707/5 |
| 6,430,558 B1 | * | 8/2002 | Delano |
| 6,438,539 B1 | | 8/2002 | Korolev et al. |
| 6,508,604 B1 | | 1/2003 | Bechmann et al. |
| 6,549,937 B1 | | 4/2003 | Auerbach et al. |
| 6,594,654 B1 | * | 7/2003 | Salam et al. ................ 707/3 |
| 6,658,431 B1 | | 12/2003 | Norman, Jr. |
| 6,676,951 B1 | | 1/2004 | Champ et al. |
| 6,709,681 B2 | | 3/2004 | Benjamin et al. |
| 6,714,916 B1 | | 3/2004 | Robertson et al. |
| 6,745,178 B1 | | 6/2004 | Emens et al. |
| 6,772,139 B1 | | 8/2004 | Smith, III |
| 6,911,687 B1 | | 6/2005 | Mandelman et al. |
| 6,947,922 B1 | | 9/2005 | Glance |
| 6,965,313 B1 | | 11/2005 | Saylor et al. |
| 7,047,202 B2 | | 5/2006 | Jaipuria et al. |
| 7,069,308 B2 | | 6/2006 | Abrams |
| 7,613,769 B1 | | 11/2009 | Hess |
| 2001/0023230 A1 | | 9/2001 | Santoku et al. |
| 2001/0053986 A1 | | 12/2001 | Dick |
| 2002/0023230 A1 | | 2/2002 | Bolnick et al. |
| 2002/0049828 A1 | | 4/2002 | Pekarek-Kostka |
| 2002/0059201 A1 | | 5/2002 | Work |
| 2002/0073075 A1 | * | 6/2002 | Dutta ................ G06F 17/30206 |
| 2002/0082919 A1 | | 6/2002 | Landau et al. |
| 2002/0091667 A1 | | 7/2002 | Jaipuria et al. |
| 2002/0116466 A1 | * | 8/2002 | Trevithick et al. ........... 709/206 |
| 2002/0123053 A1 | | 9/2002 | Luo et al. |
| 2002/0124053 A1 | * | 9/2002 | Adams et al. ................ 709/216 |
| 2002/0135614 A1 | | 9/2002 | Bennett |
| 2002/0169737 A1 | | 11/2002 | Armstrong et al. |
| 2003/0009440 A1 | | 1/2003 | Inaba et al. |
| 2003/0167324 A1 | | 9/2003 | Farnham et al. |
| 2003/0208578 A1 | | 11/2003 | Taraborelli et al. |
| 2003/0217060 A1 | * | 11/2003 | Stockton ........................ 707/10 |
| 2004/0073476 A1 | * | 4/2004 | Donahue et al. ............... 705/10 |
| 2004/0088312 A1 | | 5/2004 | Elder et al. |
| 2004/0088325 A1 | * | 5/2004 | Elder et al. ................ 707/104.1 |
| 2004/0122681 A1 | | 6/2004 | Ruvolo et al. |
| 2004/0122803 A1 | | 6/2004 | Dom et al. |
| 2004/0148275 A1 | * | 7/2004 | Achlioptas ........ G06F 17/30867 |
| 2004/0153336 A1 | | 8/2004 | Virdee et al. |
| 2004/0176993 A1 | | 9/2004 | Rajasingham |
| 2004/0215793 A1 | * | 10/2004 | Ryan et al. ................... 709/229 |
| 2005/0021630 A1 | | 1/2005 | Cannata et al. |
| 2005/0021750 A1 | * | 1/2005 | Abrams ....................... 709/225 |
| 2005/0027802 A1 | | 2/2005 | Madsen et al. |
| 2005/0080854 A1 | | 4/2005 | Madsen et al. |
| 2005/0091202 A1 | | 4/2005 | Thomas |
| 2005/0171799 A1 | * | 8/2005 | Hull et al. ........................ 705/1 |
| 2005/0198305 A1 | | 9/2005 | Pezaris et al. |
| 2005/0216550 A1 | | 9/2005 | Paseman et al. |
| 2005/0246420 A1 | * | 11/2005 | Little, II ....................... 709/204 |
| 2006/0026147 A1 | | 2/2006 | Cone et al. |
| 2006/0042483 A1 | * | 3/2006 | Work et al. ..................... 101/91 |
| 2006/0112111 A1 | | 5/2006 | Tseng et al. |
| 2006/0117378 A1 | | 6/2006 | Tam et al. |
| 2006/0218153 A1 | | 9/2006 | Voon et al. |
| 2006/0235873 A1 | | 10/2006 | Thomas |
| 2006/0259957 A1 | | 11/2006 | Tam et al. |
| 2006/0294134 A1 | | 12/2006 | Berkhim et al. |
| 2007/0112719 A1 | | 5/2007 | Reich et al. |
| 2007/0130164 A1 | | 6/2007 | Kembel et al. |
| 2007/0192461 A1 | | 8/2007 | Reich et al. |
| 2007/0214097 A1 | | 9/2007 | Parsons et al. |
| 2007/0226248 A1 | | 9/2007 | Darr |
| 2007/0245245 A1 | | 10/2007 | Blue et al. |
| 2007/0260599 A1 | | 11/2007 | McGuire et al. |
| 2008/0046458 A1 | | 2/2008 | Tseng et al. |
| 2008/0091834 A1 | | 4/2008 | Norton |
| 2008/0104225 A1 | | 5/2008 | Zhang et al. |
| 2008/0104679 A1 | | 5/2008 | Craig |
| 2008/0189621 A1 | | 8/2008 | Reich et al. |
| 2008/0189768 A1 | | 8/2008 | Callahan et al. |
| 2008/0201447 A1 | | 8/2008 | Kim |
| 2008/0255989 A1 | | 10/2008 | Altberg et al. |
| 2008/0301114 A1 | | 12/2008 | Hibbets et al. |
| 2009/0018903 A1 | | 1/2009 | Iyer |
| 2009/0070665 A1 | | 3/2009 | Chijiiwa et al. |
| 2009/0070684 A1 | | 3/2009 | Aldrich et al. |
| 2009/0070852 A1 | | 3/2009 | Chijiiwa et al. |
| 2009/0234711 A1 | | 9/2009 | Ramer et al. |

FOREIGN PATENT DOCUMENTS

| | | |
|---|---|---|
| EP | 1338967 | 8/2003 |
| JP | 04163209 | 6/2004 |
| WO | WO 99/23591 | 5/1999 |
| WO | WO 00/68860 | 11/2000 |
| WO | WO 01/16839 | 3/2001 |
| WO | WO 01/86484 | 11/2001 |
| WO | WO 03/030051 | 4/2003 |
| WO | WO 03/052621 | 6/2003 |
| WO | WO 04/061612 | 7/2004 |
| WO | WO 05/006152 | 1/2005 |
| WO | WO 05/013058 | 2/2005 |
| WO | WO 05/029362 | 3/2005 |

OTHER PUBLICATIONS

Bardon, Debbie, "Online social Networking for Business; An Interview with Konstantin Guericke Marketing VP, LinkedIn Interview", Online, Nov. 1, 2004, No. 6, vol. 28, p. 25.

Dickie, Jim, Is Social Networking an Overhyped Fad or a Useful Tool? When Put to the Test, This Sales and Marketing Application Delivers: Reality Check, CRM Magazine, Feb. 1, 2005, No. 2, vol. 9, p. 20.

Dvorak, John C., "The New Networking Crock; This is Plain, Old-Fashioned, Hopeless, Silicon Valley Utopianism at Work. Grab Hold of Your Wallets and Hold on for Dear Life!", PC Magazine.com, Feb. 11, 2004.

Frauenfelder, Mark, "Sir Tim Berners-Lee He Created the Web. Now He's Working on Internet 2.0", Technology Review, Oct. 2004, pp. 40-45.

Greenbaum, Joshua, "Cirlce of Friends: Social Networking Software Can Help Enterprises Take Advantage of Existing Relationships, Both Internally and Externally", Intelligent Enterprise, Apr. 3, 2004, p. 36.

Hamey, John, "Social Networks in Sales: Social Network Software Tells Salespeople Who in Their Organization Knows Whom Within a Company They're Trying to Sell to and Then They Can Use the Intermediary to Broker a Sale", KM World, Jun. 1, 2004, No. 6, vol. 13, p. 16.

Hicks, Matt, "Spoke Revs Hosted Enterprise Social Networking Application: The Startup Plans to Offer Spoke Workgroups in the Spring for Smaller Sales Teams That Want to Tap into Social Networking Without Deploying Software", eWeek.com, Mar. 4, 2004.

(56) References Cited

OTHER PUBLICATIONS

Hicks, Matt, "Social Networking Stretches its Reach; Two Smaller Companies Move to Integrate the Concept of Mapping Social Connections with Mobile-Phone Text Messaging and With Web Conferencing", eWeek.com, Apr. 8, 2004.
Lee, Ellen, "New 'Social Networking' Sites Help Land Jobs in San Francisco Bay Area", Contra Costa Times, Sep. 17, 2004.
Padgett, Lauree, "Networking, Migrating and Aggravating: In Other Words, Discusses Migrating Library Systems, Malware Tools, Social Networking", Information Today, Mar. 1, 2004, No. 3, vol. 21, p. 40.
Pankhurst, Steve, "Social Networks Run on Trust, as Do We at Friends Reunited", Revolution, Feb. 9, 2004, p. 13.
Schofield, Jack, "Software to Help You Network", Computer Weekly, Mar. 16, 2004, p. 32.
Smith, Philip, "Marketing Promise of Social Sites", Revolution, Apr. 21, 2004, p. 17.
International Search Report for WO 2006/036165 (Application No. PCT/US04/38064); dated Mar. 9, 2006.
International Search Report for WO 2006/036187 (Application No. PCT/US05/06617); dated May 8, 2007.
International Search Report for WO2006/036216 (Application No. PCT/US05/15952); dated Aug. 25, 2006.
International Search Report for WO2006/041425 (Application No. PCT/US04/30259); dated May 30, 2006.
International Search Report for WO2006/055555 (Application No. PCT/US05/41349); dated Jun. 1, 2006.
International Search Report for WO2006036186 (Application No. PCT/US2005/005847); dated Apr. 21, 2006.
International Search Report for WO2007005463 (Application No. PCT/US06/25166); dated Dec. 14, 2007.
International Search Report for WO2007016252 (Application No. PCT/US06/29210); dated Jul. 13, 2007.
Written Opinion for WO 2006036187 (Application No. PCT/US05/06617); dated May 8, 2007.
Written Opinion for WO2006036216 (Application No. PCT/US05/15952); dated Aug. 25, 2006.
Written Opinion for WO2006041425 (Application No. PCT/US04/30259); dated May 30, 2006.
Written Opinion for WO2006055555 (Application No. PCT/US05/41349; dated Jun. 1, 2006.
Written Opinion for WO2006036165 (Application No. PCT/US04/38064); dated Mar. 9, 2006.
Written Opinion for WO2007005463 (Application No. PCT/US06/25166); dated Dec. 14, 2007.
Written Opinion for WO2007016252 (Application No. PCT/US06/29210); dated Jul. 13, 2007.
Written Opinion for WO2006036186 (Application No. PCT/US2005/005847); dated Apr. 21, 2006.
"A Model of Network Capitalism: Basic Ideas and Post-Soviet Evidence", Journal of Economic Issues, Mar. 2004, vol. 38, No. 1, pp. 85-111 Mar. 2004, 85-111.
"Google search", Google search of "totally random keywords", May 14, 2009.
Bardon, Debbie, "Online Social Networking for Business: An Interview with Konstantln Guericke Marketing VP, LinkedIn Interview", Online, Nov. 1, 2004, No. 6, vol. 28, p. 25.
Dickie, Jim, "Is Social networking an Overhyped Fad or a Useful Tool? When Put to the Test This Sales and Marketing Application Delivers: Reality Check", CRM Magazine, Feb. 1, 2005, vol. 9, p. 20.
Dvorak, John C., "The New Networking Crock: This is Plan, Old-Fashioned, Hopeless, Silicon Valley Utopianism at Work. Grab Hold of Your Wallets and Hold on for Dear Life!"; PC Magazine.com, Feb. 11, 2004.
Fitzgerald, Michael, "Internet Working"; Technology Review, Apr. 1, 2004, vol. 107, No. 3, p. 44.
Frauenfelder, Mark, "Sir Tim Barners-Lee He Created the Web. Now He's Working on Internet 2.0"; Technology Review, Oct. 10, 2004, pp. 40-45.
Gathier, Chris, "West Coast 'Social Networking' Web Sites Attract Users, Investors"; Boston Globe, Dec. 7, 2003.
Greenbaum, Joshua, "Circle of Friends: Social Networking Software Can Help Enterprises Take Advantage of Existing Relationships, Both Internally and Externally; Enterprise Applications"; Intelligent Enterprise, Sec. 5, vol. 4, Apr. 3, 2004, p. 36 Apr. 3, 2004.
Harney, John, "Social Networks in Sales: Social Network Software Tells Salespeople Who in Their Organization Knows Whom Within a Company They're Trying to Sell to and Then They Can Use the Intermediary to Broker a Sale"; KM World, Jun. 1, 2004, No. 6, vol. 16.
Herman, Jim, "The New Science of Networks", Business Communications Review, Jun. 1, 2003. No. 6, vol. 33, p. 22.
Hicks, Matt, "Social Networking Stretches Its Reach; Two Smaller Companies Move to Integrate the Concept of Mapping Social Connections with Mobile-Phone Text Messaging and with Web Conferencing"; Ziff Davis Media, EWeed.com, Apr. 8, 2004.
Hicks, Matt, "Spoke Revs Hosted Enterprises Social Networking Application: The Startup Plans to Offer Spoke Workgroups in the Spring for Smaller Sales Teams that Want to Tap into Social Networking Without Deploying Software"; eWeek.com, Mar. 4, 2004.
Lee, Ellen, "New 'Social Networking' Sites Help Land Jobs in San Francisco Area", Lee; Contra Costa Times, Sep. 17, 2004.
Markus, Michael J., "Collection of Linked Databases"; Office Action issued in U.S. Appl. No. 11/686,416.
Markus, Michael J., "Collections of Linked Databases"; Final Office Action issued in U.S. Appl. No. 11/686,416.
Markus, Michael J., "Collections of Linked Databases"; Non-Final Office Action issued in U.S. Appl. No. 11/686,409.
Markus, Michael J., "Collections of Linked Databases"; Final Office Action issued in U.S. Appl. No. 11/686,409.
Markus, Michael J., "Collections of Linked Databases"; Final Office Action issued in U.S. Appl. No. 11/686,429.
Markus, Michael J., "Collections of Linked Databases"; Office Action issued in U.S. Appl. No. 11/686,429.
Markus, Michael J.; "Collections of Linked Databases and Systems and Methods for Communicating About Updates Thereto"; Non-Final Office Action issued in U.S. Appl. No. 11/989,039.
Markus, Michael J., "Social Network Analysis"; Final Office Action issued in U.S. Appl. No. 11/686,401.
Markus, Michael J., "Social Network Analysis"; Office Action issued in U.S. Appl. No. 11/686,401.
McGuire, Heather A., "Social Network Analysis"; Final Office Action issued in U.S. Appl. No. 11/686,394.
McGuire, Heather A., "Social Network Analysis"; Office Action issued in U.S. Appl. No. 11/686,394.
Padgett, Lauree, "Networking Migrating and Aggravating: In Other Words, Discusses Migrating Library Systems, Malware Tools, Social Networking", Padgett, Lauree, "Networking, Migrating and Aggravating: In Other Words, Discusses Migrating Library Systems, Malware Tools, Social Networking", Information Today, Mar. 1, 2004, No. 3, vol. 21, p. 400.
Pankhurst, Steve, "Social Networks Run on Trust, as Do We at Friends Reunited", Pankhurst, Steve, "Social Networks Run on Trust, as Do We at Friends Reunited", Revolution, Feb. 9, 2004, p. 13.
Schofield, Jack, "Software to Help You Network", Schofield, Jack, "Software to Help You Network", Computer Weekly, Mar. 16, 2004, p. 32.
Smith, Philip, "Marketing Promise of Social Sites", Smith, Philip, "Marketing Promise of Social Sites", Revolution, Apr. 21, 2004, p. 17.
Solheim, Shelley, "Let's Keep in Touch: Social Network Tools Take Air at Enterprise Sales."; eWeek, News & Analysis, Mar. 29, 2004, p. 31.
Solheim, Shelley, "Social-Networking Vendors Set Their Sights on the Enterprise"; eWeek.com, Mar. 19, 2004.
Solomon, Marc, "Searching Becomes Conversing: Social Networking Application for Sales, Recruiting, etc."; Searcher, Mar. 1, 2004, No. 3, vol. 12, p. 16.

(56) References Cited

OTHER PUBLICATIONS

Topper, Elisa F., "Working Knowledge: Putting Networks to Work: Professional Development"; American Libraries, Dec. 1, 2003, No. 1.1, vol. 34, p. 88.

Whaley, Charles, "Six Degrees of Separation Takes on an Electronic Spin: Social Networking via the Web is All the Rage, and Venture Capitalists of Throwing Handfuls of Money at Startups"; Computing Canada, Mar. 26, 2004, No. 4, vol. 30, p. 13.

\* cited by examiner

Results of Your Search

Physician, drug, institution, keyword, subject or any other search term(s)

piriformis syndrome

Tips...

Seek Again

| 1st Degree (Your Colleagues) | 2nd Degree (Your Colleagues' Colleagues) | 3rd Degree (And Beyond) | 4th Degree (And Beyond) |
|---|---|---|---|
| Ann K. Smith | Thomas D. Patrick | Steven S. Perry | Derek C. Smoltz |
| Ann R. Smith | Steve L. Miola | Ed. L. Blue | |
| Seth L. Craig | Suzanne K. Mitchell | Beverly T. Simon | |
| Seth L. Craig | Melissa K. Bean | Randal A. Ellison | |
| David K. Brown | Thomas D. Patrick | | |
| Ann K. Smith | Amy I. Dolimi | | |
| Seth L. Craig | Lynette R. Morrison | | |
| Seth L. Craig | | | |

Currently Logged in as: Michael J. Markus
Log Out

Search | Message Center | Invitations (2 Pending) | Settings | Help

Figure 15

COLLECTIONS OF LINKED DATABASES

CROSS-REFERENCE TO RELATED APPLICATIONS

This application is a continuation of PCT application PCT/US2005/041349, filed on Nov. 15, 2005, now published as WO 2006/055555, which claims priority to PCT application PCT/US2004/038064, filed on Nov. 15, 2004, now published as WO 2006/036165, and to PCT application PCT/US2005/0006617, filed on Mar. 2, 2005, now published as WO 2006/036187. These three prior applications are hereby incorporated into the present application by reference.

FIELD

The technology described in this patent document is generally directed to a system or method for searching a collection of databases in order to identify at least one database in the collection that has or is likely to have information on a topic. More specifically, the technology is directed to a system or method for performing a directed search on a collection of linked databases in order to identify at least one database in the collection that has or is likely to have data on a topic. Further, the technology is directed to a system or method for performing a directed search of a social network in order to identify at least one social-network member that has or is likely to have information on a topic.

The technology described herein is also directed to making and using inferential networks. Further, the invention is directed to making inferential networks using data generated from directed searches of collections of linked databases.

BACKGROUND

When seeking information, many people rely upon sources such as the internet, intranets, pamphlets, magazines, and advertisements to provide them with adequate information and ultimately to aid in their decision-making process. In their searches, however, such sources often include barriers that prevent people from acquiring the valid, reliable and useful information they need. Notably, the anonymity of interconnected computer networks (e.g., the internet) prevents people from trusting the reliability of the information source. Clearly, most people would rather consult their friends and colleagues that they know and trust on a first name basis—or knowledgeable people that they know through their friends and colleagues—when seeking the answer to a particular question. For example, it is well known that informal communication via personal communication networks allows decision makers to reduce the uncertainty regarding unfamiliar technologies and/or products by questioning and consulting trusted others. Posing questions to the members of one's personal communication network allows individuals to obtain first, second, and third-hand accounts from individuals they know directly or through intermediaries. Theoretically, the varied experiences of one's network of peers, acquaintances, and people connected to the person through countless others should more than adequately serve to answer one's questions. Unfortunately, experiential and other knowledge can be difficult to procure; because people are unaware of who in their interpersonal network has experience or information regarding the information they seek, informal searches for advice can seem arbitrary, unfocused, and inefficient. The absence of a formal map or knowledge of communication structure prevents the person from realizing the full potential of the collective IQ of his network of friends and colleagues.

Social network analysis is known and has been described as the mapping and measuring of relationships and flows between people, groups, organizations, computers, or other information knowledge processing entities.

Social network analysis (SNA) can be used to generate data and draw conclusions based upon the flow of information (or other resources) within a social network. SNA maps the relationships of people within a social network in order to monitor, understand, and utilize the informational flow within the network—who do people get their information from and who do they give it to? A social network is distinct from an organizational chart because the organizational chart shows formal relationships—who works where and who reports to whom. On the other hand, a social-network-analysis map shows more informal relationships—who knows who and who do they share information with. SNA therefore facilitates visualizing and understanding personal relationships that can either facilitate or impede knowledge creation and sharing.

While social network analysis is known, little has been done to streamline its use in an effort to maximize its potential. Further, implementations of social-network analysis have yet to be fully explored. Specifically, most individuals interested in social network data have merely conducted interviews or surveys to obtain the data, and they have then kept the conclusions drawn from such data exclusively in the world of academia. For example, sociologists who studied the diffusion of hybrid seeds through the social networks of farmers in Iowa published their findings in academic journals. They did not, however, disclose the conclusions that they reached based on the analysis of their data to the general public.

SNA is gaining popularity in the field of marketing in order to facilitate the diffusion of innovations (e.g., new products) through customer networks. To this end, a number of companies have conducted preliminary data analyses using SNA in an attempt to map customer networks and determine who most customers contact for advice within a particular domain. In theory, if a company can identify and market to the small percentage of people that make up the opinion leadership or opinion leaders within a given customer network, they can lower both the cost of marketing and the time it takes for the innovation to diffuse through the customer network. Marketing departments are therefore anxious to identify "opinion leaders" within a given field. Such individuals are often highly connected "hubs" within a social network web, and they are important targets for marketing because other members in the customer network often go to them for advice regarding the latest trends and innovations. Clearly, the ability to selectively target opinion leaders, which may cut advertising and marketing costs while simultaneously increasing the effectiveness of marketing messages, would be highly beneficial. However with current technology, collecting, mapping, and identifying what role each potential customer plays within a given network demands considerable time, effort, and money—making such an approach prohibitive to all but a few companies.

While companies first demonstrated interest in the utility of SNA for targeted marketing in the 1950's, prior-art technology is slow and cumbersome. Most recently in the pharmaceutical domain, some pharmaceutical companies gathered relational information within the medical field by sending a two-page survey to approximately 800,000 physicians in the United States. The pharmaceutical companies paid each participating physician approximately $250 for their time, but the survey yielded only a 5% to 8% response rate—this equates to a one time $10,000,000 to $16,000,000 data-collection procedure. Further limitations on the accuracy or utility of such a strategy include the "static" nature of a one-time survey that fails to capture the dynamic nature of social networks.

Additional prior-art methods for performing SNA exist. One prior art method attempts to draw an inference on who is well known and influential within the field of medicine based on general publications, conference presentations and disclosures. This prior-art method is clearly limited in its lack of a social-network map that clearly depicts the informal and formal communication links between physicians. In other words, the approach is lacking because the data does not directly and clearly correspond to advice, influence, or communication among physicians. Clearly, a new approach to the collection of reliable, valid, meaningful, and cost-effective social-network data is needed.

In the domains of leisure and entertainment, parlor games such as "Six Degrees of Kevin Bacon" and websites such as "Friendster" and "LinkedIn" have demonstrated the ability of an internet system to create social networks of friends and business associates for the purposes of making friends, finding dates, identifying potential job candidates, and seeking employment. A major drawback of such popular social-network sites, however, is the seemingly arbitrariness of the links between users. Allowing "friends" to link to one another in a situation that almost promotes competition to score high volumes of links creates a chaotic environment wherein the context, strength, or value of relationships between users cannot be ascertained. Arbitrary links undermine the utility of social networks that purport to connect people to trustworthy second and third-degree contacts premised upon mutual "friends." Therefore, the data captured and utilized by these websites is highly unreliable. Because the websites have not set parameters, guidelines, or norms to govern or define the links between users, the social networks generated by these sites provide limited aid to users and are nearly useless to parties interested in using social-network data for their own purposes.

Previous methods for inviting new people into social networks online or indicating first-degree contacts via a survey typically lack the sophistication to accurately capture the directionality of an established social-network link. It is generally known that social-network links can be either unidirectional (e.g., from A to B) or bi-directional (e.g., from A to B and from B to A). Capturing reliable, valid, and meaningful social-network data typically necessitates the directionality of the links within a social-network. Establishing and recording accurate directionality information about social-network links increases both the meaning and utility of a social-network map and social-network data generated therefrom. Prior-art methods for inviting (or listing) people into a social network often erroneously or prematurely infer bidirectional relationships—and misinterpretation of the directionality of a link leads to misleading information.

More specifically, prior-art methods directed to determining the directionality of social-network links do not provide a way to confirm the actual existence of a unidirectional or bi-directional link. For example, in the prior art, a first person will typically declare that a second person is linked to the first person, and as a result, the second person is incorporated into the first person's social network as a unidirectional or bi-directional link. Note that the prior-art methods don't provide for a way to confirm the existence or directionality of the link. In other words, the prior art doesn't provide for a method by which the second person can confirm or deny the relationship that the first person has alleged. Further, if a first person listed a second person as a member of the first person's social network, then the prior art doesn't provide a way to consult the second person as a way to confirm the relationship. The art therefore needs a more accurate method for determining the directionality of a social-network link.

Earlier internet search engines are typically designed to match search criteria—general words, names, phrases, etc.—with a list of "best fit" websites, based upon keywords and the popularity of the websites. The recent application of social networks to such search engines has introduced the concept of including evaluation of websites by an individual's contacts in the ranked presentation of the "best fit" websites. There still, however, remains a need in the art for an electronic search engine that can both: identify individuals in a field of interest that have knowledge regarding the searched topic and how the searcher is connected through a set of intermediaries to the individual that possesses the knowledge, and allows the searcher to ascertain the degree to which the person and information can be trusted.

Prior-art methods for performing broadcast searches of data are well known. And broadcast searching is widely used in many areas of technology today. Broadcast searching can generally be described as a search method that searches all available searchable data in an effort to locate the sought-after data. Broadcast searching can be slow and cumbersome, and there is therefore a need in the art for an additional search method for searching collections of databases and social networks.

SUMMARY

In accordance with the teachings described herein, systems, devices and methods are provided for conducting a search of a network for information related to a topic specified by a search initiator. A query may be generated that includes search information and a first-degree contact. The first-degree contact may be an electronic record in a database that represents a physician, and the search information may identify the medical topic. One or more databases may be searched using the query to identify one or more physicians who are identified in connection with the medical topic and who are directly or indirectly associated with the first-degree contact.

The present invention further provides a method of conducting a search of a social network for information related to a topic specified by a search initiator. The method includes the steps of generating a query that includes a search string related to the topic and a first-degree contact of the search initiator, wherein the first-degree contact is a database in the search initiator's personal communication network that is directly linked to the search initiator and is represented by an electronic record. Additional aspects of the method optionally include defining a portion of the search initiator's personal communication network as including one or more databases that are eligible to be returned as a search result; and searching an electronic profile representing one or more databases using the query to identify a database in connection with the topic that is directly, indirectly, or both directly and indirectly associated with the first-degree contact.

Other aspects of the present invention provide a system for conducting a search of a social network for information related to a topic specified by a search initiator. The system includes a network that includes a server in communication with a remotely-located terminal over a communication channel. At least one of the server and the terminal includes computer-executable instructions for generating a query that includes a search string related to the topic and a first-degree contact of the search initiator, wherein the first-degree contact is a database in the search initiator's personal communication network that is directly linked to the search initiator and is represented by an electronic record. At least one of the server and the terminal also optionally includes computer-executable instructions for defining a portion of the search initiator's personal communication network as including one or more databases that are eligible to be returned as a search result; and computer-executable instructions for searching an electronic profile representing one or more databases using the query to identify a database in connection with the topic that is directly, indirectly, or both directly and indirectly associated with the first-degree contact.

Yet other aspects of the present invention provide a computer-readable medium having computer-executable instructions for performing a method of conducting a search of a social network for information related to a topic specified by a search initiator. The method to be performed according to the instructions includes the steps of generating a query that includes a search string related to the topic and a first-degree contact of the search initiator, wherein the first-degree contact is a database in the search initiator's personal communication network that is directly linked to the search initiator and is represented by an electronic record. The method further includes defining a portion of the search initiator's personal communication network as including one or more databases that are eligible to be returned as a search result; and searching an electronic profile representing one or more databases using the query to identify a database in connection with the topic that is directly, indirectly, or both directly and indirectly associated with the first-degree contact.

BRIEF DESCRIPTION OF THE DRAWINGS

FIG. 7 is an illustrative depiction of a search interface for initiating a broadcast search displayed by a display device;

FIG. 9 is an illustrative depiction of a search interface for initiating a directed search, said interface being displayed by a display device;

FIG. 15 is an illustrative depiction of a search-results interface displayed by a display device to present the results of a directed search to a search initiator.

DETAILED DESCRIPTION

Figure 1:
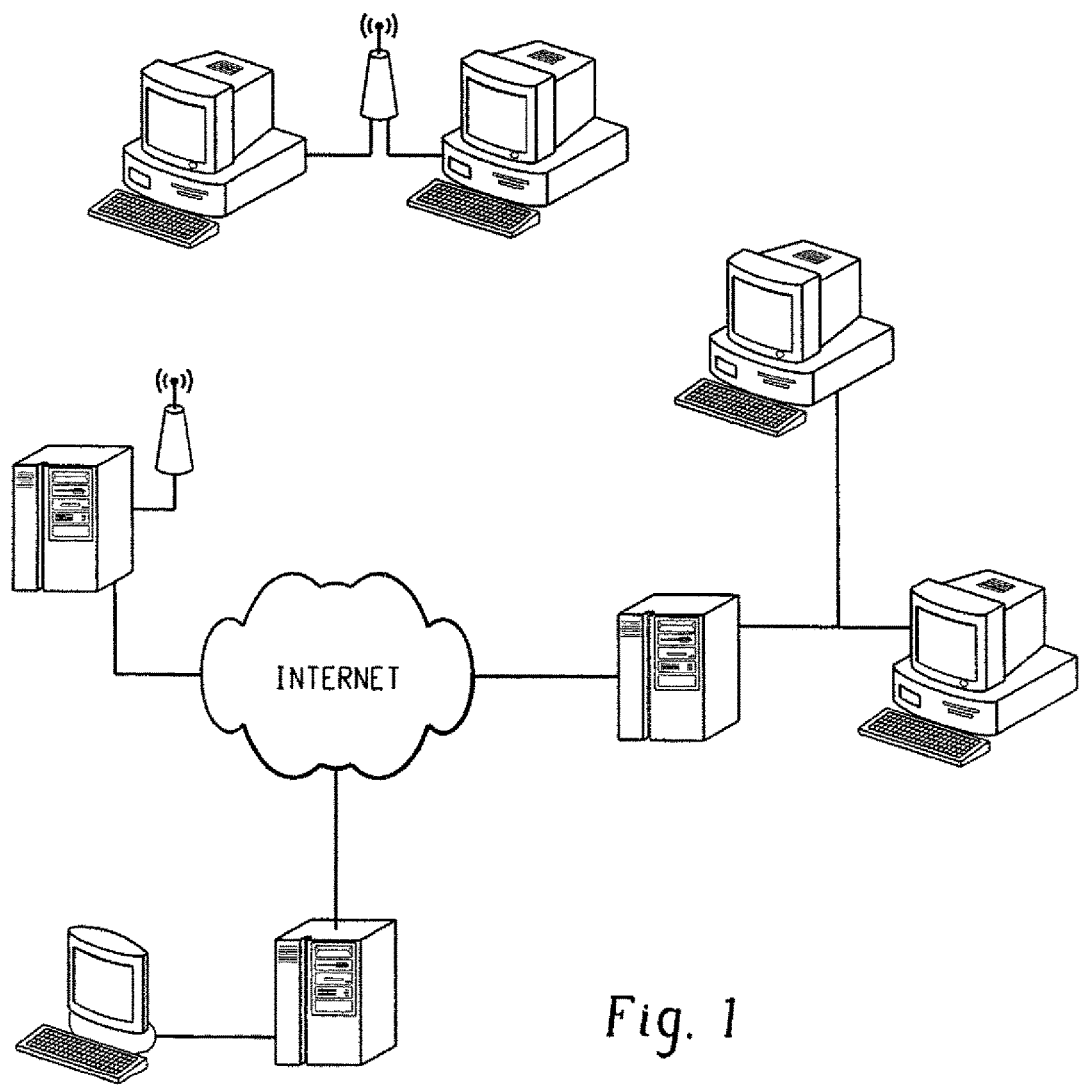
FIG. 1 is an illustrated arrangement of a network for employing a system for searching a collection of linked databases.

The technology described herein is generally directed to a system for, and a method of searching a collection of linked databases. In one example, the system and method can be utilized with an electronic network, such as that shown schematically in FIG. 1. As illustrated in FIG. 1, a plurality of computer terminals can communicate over a network, which, in the illustrated example is the Internet. File servers can store electronic information representing electronic pages commonly referred to as webpages or websites that can be retrieved and displayed by each remotely-located computer via the Internet. A file server is an electronic storage device that provides remotely located terminals on a network with controlled access to shared resources. For example, a server can simply be a computer or other device that manages network resources such as hard drives and other electronic memory devices, while the remote terminal can be a notebook computer, desktop computer, cell phone, personal digital assistant, or any other device capable of communicating with the network.

As is well known in the art, users of remotely-located computer terminals can access webpages via a network connection to the Internet, for example, by entering the appropriate uniform resource locator ("URL") into a web browser. The URL is associated with a particular address on the network from where the webpage the user wishes to view can be retrieved. Web browsers, such as Internet Explorer® produced by Microsoft®, are also well known computer software packages for viewing documents conforming to the hyper text markup language, commonly referred to as HTML. In use, the web browser is launched on the computer terminal to present the user with a graphical user interface facilitating the entry and display of electronic data transmitted over the network.

A social network comprises a network of databases, some of which are related or linked to other databases within the social network, either directly, indirectly or both. The relationships between databases within the social network can also be categorized with regard to one or more particular topic(s). A database, as used herein, is a person, website, journal article, hospital, corporation, or any other entity that could possess information about one or more topics that is being sought by a member of the social network. Each database can be represented in the social network by a webpage or electronic profile that is electronically searchable. The profile can include personal information, professional information, educational information, geographic information, corporate information, any other type of information, and any combination thereof about each respective database.

Within a social network there are a plurality of personal communication networks ("PCNs"). A PCN is contrasted with the social network in that the social network comprises all physicians (i.e., databases) that have been invited or who have otherwise signed up to be included in the entire population of physicians (or databases), regardless of who they are linked, or otherwise related to. In contrast, a physician's PCN includes that portion of the entire social network to which the physician is linked or related to, either directly or indirectly. In other words, the social network is considered to be the general population of all network members (also referred to as databases) and a database's PCN is a subset of the social network to which the database is linked, indirectly, or a combination thereof by one or more communication links. It should be understood, however, that in other examples a database's PCN could include all members of the social network. A detailed description of how a database can be linked or related to another database is provided below.

It is worth noting at this point, however, that the communication links discussed herein are typically not tangible, uninterrupted channels of communication. Instead, the communication links represent an electronic record of a relationship between a first database and other database(s) who have been invited to join the first database's PCN. The existence of the communication links merely serves as an electronic record to identify the trusted colleague(s) and other database(s) of a database. The communication links can also optionally be defined as pertaining to one or more particular contexts or topics.

The method, system and computer-executable instructions described herein can find application in a large variety of fields and professions, such as the medical, legal, architectural, mechanical, chemical, electrical, automotive fields, and the like. However, for purposes of clearly describing various embodiments, examples are employed below where all the databases in the social network are physicians. Thus, a first database in the medical social network is a physician, and said first physician will be linked by a communication link to other physicians who make up the first physician's PCN. But again, it should be clear that alternate embodiments exist where a database could be a hospital, a corporate client, an insurance company, and any other entity aside from a physician.

The social network of physicians described herein can optionally be a formal social network, requiring each physician in the social network to be first invited to join, and second, verified as being licensed by a certifying agency (the American Medical Association in this example) before being permitted to join the social network. To initially create the social network, however, one or more "seed" physicians can be established by a social-network administrator as the initial members of the medical social network without first requiring an invitation. Thus, each seed physician can extend invitations to other physicians to join the social network, these later-invited physicians can then extend invitations to yet other physicians, and so on.

Computer-readable logic can be used to facilitate the invitation-and-acceptance method of a formal social network. Once a seed physician has been established, the seed physician can launch a web browser on a computer terminal that is connected to a wide-area network, such as the Internet. The seed physician enters a suitable URL into the web browser that causes the web browser to access and display a login webpage generated by computer-readable logic from a remote file server. The login webpage requires the seed physician to enter data that verifies the identity of the seed physician before allowing the seed physician to access restricted webpages generated by computer readable logic. The restricted webpages present a graphical user interface that allow the seed physician to access social-network data and create, edit, amend, and otherwise manipulate at least part of the social network data. The data entered via the graphical user interface can be manipulated by a computational platform such as a server, the computer terminal the seed physician is using, and any other computational platform to display relevant social network data as described in detail below.

Figure 2:
FIG. 2 is an illustrative depiction of a new-invitation interface displayed by a display device.

To become a member of the social network, a physician can optionally be required to receive and accept an invitation to join, or the physician can otherwise be entered into the social network either on a voluntary basis or by a network administrator. In this manner, the number of unauthorized individuals populating the social network and PCNs is minimized. Computer-readable logic can facilitate the invitation and acceptance process for developing social network and PCN members. FIG. 2 provides an illustrative embodiment of one of the restricted webpages 35 that can be generated by computer readable logic as part of this process.

The webpage 35, being displayed by a display device in the form of a computer monitor 37, identifies the seed physician 39 logged into the social network, which, in this embodiment is Mike Markus. One or more seed physicians 39 may be established to initially populate the social network since all subsequent members of the social network may optionally need an invitation from current members of the social network to join. This can be done by allowing a network administrator to randomly select each seed physician 39, select one or more seed physician(s) 39 based on their status relative to other physicians with regard to a particular topic, or select the seed physician(s) 39 based on any other criteria or combination thereof. However, it should be noted that other embodiments exist where physicians can voluntarily enroll as members of the social-network without first being invited. For such embodiments, the voluntarily-enrolling physicians can still be subjected to an authorization process that verifies their status as a physician or other database authorized to join the social network, as discussed above. But to clearly describe the technology, the detailed discussion below will be limited to the embodiments requiring a physician to be invited to join the social network.

The webpage shown in FIG. 2 is a new-invitation interface 35, and includes a name-entry field 42 to permit the seed physician 39 to input data identifying the physician (invitee) who the seed physician 39 would like to invite to join the seed physician's PCN. The new-invitation interface 35 in FIG. 2 also includes a contact-information field 45 to allow the seed physician 39 to enter the e-mail address or other electronic contact information or ID of the invitee. As shown in FIG. 2, the data identifying the invitee is the invitee's first and last names, while the electronic contact information is the invitee's e-mail address. All of this data is to be entered according to the embodiment shown in FIG. 2 into text-entry fields that allow the seed physician 39 to type the desired data to be entered. For this embodiment, the fictitious first name (Steven), last name (Johnson), and e-mail address (sjohnson@anyhospital.com) were entered to identify the invitee, and to specify the e-mail address to which notice of the invitation will be sent.

Although shown as text-entry fields, the data-entry mechanisms can be any data-entry mechanism, including but not limited to a drop-down menu, radio buttons, check boxes, and any other type of data-entry mechanism. Further, electronic contact information other than an e-mail address such as an instant messenger ID, for example, can be specified to identify the location where notice of the invitation is to be sent to the invitee.

The seed physician 39 is also presented with the opportunity to specify the context of the invitation that is to be sent to the invitee. In the graphical user interface shown in FIG. 2, the seed physician 39 is presented with a context menu 48 of available contexts 51 from which to select the context 51 of the invitation, and any resulting communication link. The available contexts 51 from which the seed physician 39 can select in FIG. 2 include Diagnostics, Treatment, Pharmacological, Research, Education and Practice Management, but contexts 51 other than those listed here are also possible. Further, the contexts may be varied based on the profession for which the technology is utilized. Thus, in the field of auto repair, for example, the available contexts 51 can include Diagnostics, Electrical, Body, Engine, Transmission, Suspension, and Interior.

Any context 51 specified by the seed physician 39 via the new-invitation interface 35 when creating the invitation to be sent to the invitee may indicate the context 51 about which the seed physician 39 wishes to communicate with the invitee. Thus, if the seed physician 39 selects Diagnostics from the menu 48, for example, then the communication link that is formed if the invitee accepts the invitation may include an electronic record that the seed physician 39 consults with the invitee (who is now a member of the seed physician's PCN) about diagnostics. Further, the relatively broad contexts 51 listed in the menu 48 can optionally include subtopics that serve to narrow the scope of the contexts 51. For instance, the context 51 "Diagnostics" can include the subtopic "cancer." In that case, the context 51 of any resulting communication link between the seed physician 39 and the invitee would be in the context 51 of cancer diagnostics.

Also shown in FIG. 2 is the reciprocal-context menu 53 that permits the seed physician 39 to enter into the system whether the seed physician 39 wishes to automatically accept a reciprocal invitation. If the seed physician 39 does elect to automatically accept a reciprocal invitation, he or she can optionally also specify the reciprocal context(s) 56 about which the seed physician 39 feels comfortable being consulted, Similar to the discussion above, any reciprocal context(s) 56 specified by the seed physician 39 via the new-invitation interface 35 when creating the invitation to be sent to the invitee may indicate the context(s) 56 about which the seed physician 39 feels most comfortable providing information. Thus, if the seed physician 39 selects Research from the reciprocal-context menu 53, for example, then any communication link that is formed if the invitee sends a reciprocal invitation may also include an electronic record that the invitee consults with the seed physician 39 (who would then become a member of the invitee's PCN) about research. And again, the relatively broad reciprocal contexts 56 listed in the reciprocal-context menu 53 can optionally include subtopics (not shown) that serve to narrow the scope of the reciprocal contexts 56.

The reciprocal contexts 56 displayed in the reciprocal-context menu 53 can be the same as the contexts 51 listed in the menu 48, they can differ from the contexts 51 listed in the menu 48, and both the contexts 51 and reciprocal contacts 56 can be customized by the seed physician 39 as desired.

Electronic selection of the "Send Invitation" button 58 by the seed physician 39 in FIG. 2 causes execution of computer-executable logic that transmits a notice of a pending invitation to the invitee at the location entered into the contact-information field 45. For the embodiment shown in FIG. 2, the notice of a pending invitation will be an e-mail sent to the invitee's e-mail address specified in the electronic contact field in FIG. 2. The notice of a pending invitation can optionally include a hyperlink that will take the invitee to a registration-interface webpage (not shown) of the present system that is generated according to instructions embodied by computer-readable logic. The registration-interface webpage allows the invitee to enter information about himself for any verification purposes and to create an electronic record to represent the invitee in the social network once the invitee is successfully registered. The data entered by the invitee can optionally be updated, amended, and supplemented after the initial registration is complete as desired by the invitee. A hyperlink is a reference (or link) typically written in HTML from some point in one hypertext document to some point in another document or another place in the same document. When electronically selected, the hyperlink jumps to the target document or location. The registration interface displays an electronic form to be completed by the invitee that collects data to be included in the invitee's electronic profile. The electronic form may be completed before allowing the invitee to accept the invitation, decline the invitation, or accept the invitation from the seed physician 39 and send a reciprocal invitation.

One piece of information that may be requested in the electronic form of the registration interface is the invitee's medical education number assigned to each physician by the American Medical Association ("AMA") when they become licensed to practice medicine in the United States. When the invitee has indicated that the electronic form is complete, selection of a "Register" button can execute computer-executable logic that will compare the registration number entered by the invitee to an electronic library that includes all registered physicians and their respective registration number. This comparison is performed to minimize the number of unauthorized individuals who join the social network.

Although the AMA-issued registration number is one method of verifying whether an invitee is authorized to join the social network, the technology described herein can use any form of authorization, based on any type of certification. For example, the technology can compare the license number issued by the Canadian Medical Association to a physician licensed to practice medicine in Canada, and the like. Or, the computer-readable logic can compare the invitee's name to a roster of individuals who work for a particular hospital and are authorized to join the social network. In such an embodiment, the name of the hospital roster to use for said comparison can be determined automatically by the system without user intervention based on the domain in the e-mail address or other electronic contact information entered by the seed physician 39 in the contact-information field 45.

Figure 3:
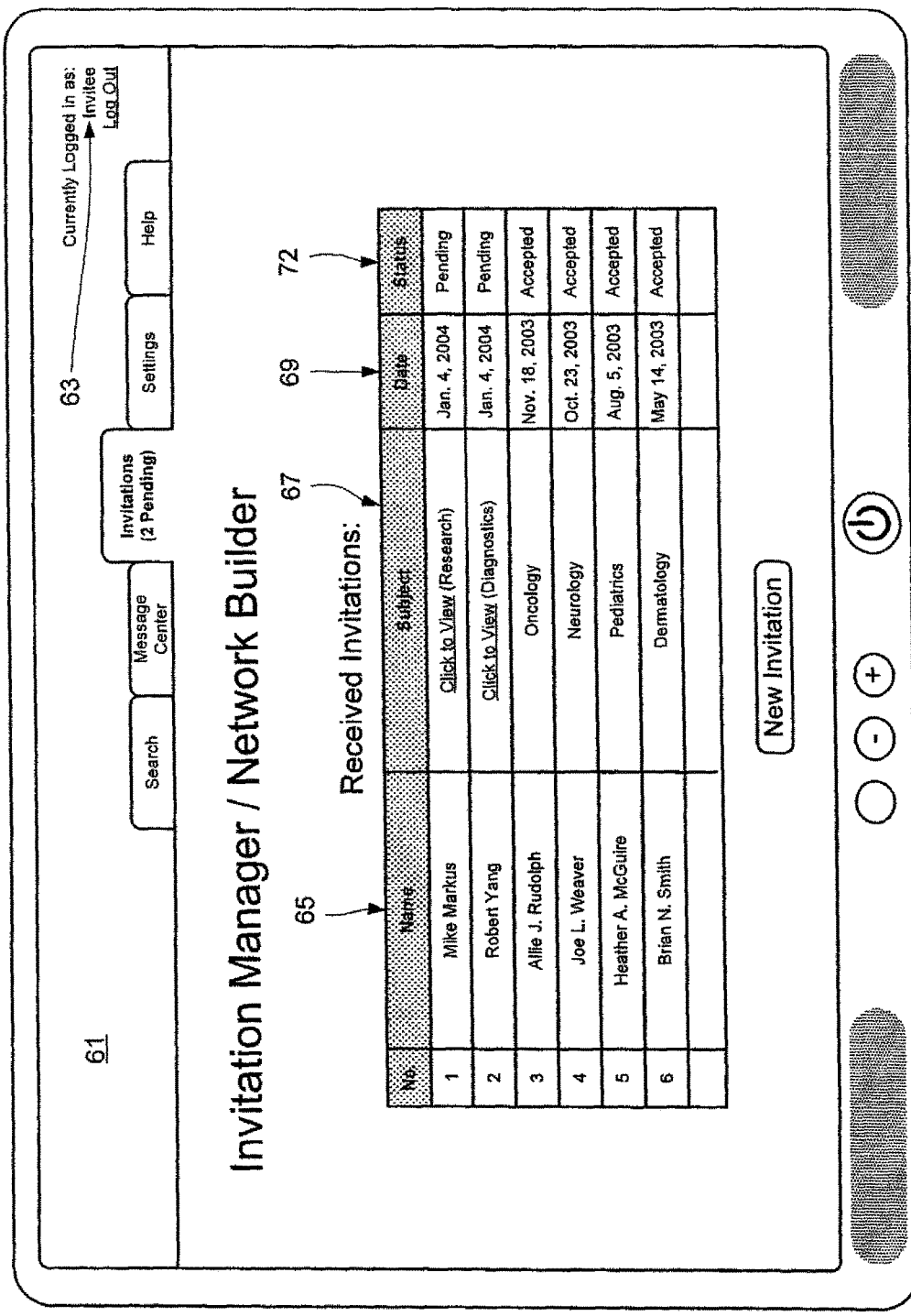
FIG. 3 is an illustrative depiction of an invitation-management interface displayed by a display device.

Upon completion of the electronic form displayed as part of the registration interface, and assuming verification of the invitee's status to join the social network, the invitee becomes a member of the social network, is logged into the system, and is presented with an invitation-management interface 61, which is shown in FIG. 3. The invitation-management interface 61 is also generated from computer-readable instructions, and displays the invitee's name 63 as the current user, just as the seed physician's name 39 was in FIG. 2.

The invitation-management interface 61 displays information informing the current user (who will still be referred to as the invitee for the sake of clarity) about invitations that have been received from other network members. In FIG. 3 the information displayed includes columns of physicians 65 who extended an invitation to the invitee; the context 67 of each invitation, if specified; the date 69 each invitation was received; and the status 72 of each invitation. Information about the invitation from the seed physician 39 (Mike Markus) discussed above can be seen in the first row of the table in FIG. 3. The other invitations are included merely as examples of the types of information that can be displayed, and represent invitations received by the invitee from other members of the social network.

Figure 4:
FIG. 4 is an illustrative depiction of a response interface displayed by a display device.

Electronically selecting the hyperlink reading "Click to View" in the first row of the table in FIG. 3 corresponding to the invitation received from the seed physician 39 (Mike Markus) causes execution of computer-readable logic to display the response interface 75 of FIG. 4. The response interface 75 is also a webpage retrievable over the Internet. From the response interface 75, the invitee can select from a plurality of options, which include: accept the invitation and extend a reciprocal invitation to the seed physician 39 who invited the invitee (labeled 77); accept the invitation from the seed physician 39 without extending a reciprocal invitation (labeled 79); and decline the invitation from the seed physician (labeled 81).

The option to accept the invitation from the seed physician 39 and extend a reciprocal invitation establishes the invitee as a member of the seed physician's PCN, and allows the invitee to invite the seed physician 39 to become a first-degree contact of the invitee's PCN. The invitee's acceptance establishes the invitee as a first-degree contact in the seed physician's PCN and causes execution of computer-executable instructions to record said membership in a computer-readable medium, along with the relationship of the invitee relative to the seed physician 39 as described in detail below. The method for extending the reciprocal invitation is analogous to that followed to extend the invitation from the seed physician 39 to the invitee. However, since the seed physician 39 is obviously already a member of the social network, the seed physician 39 is not required to enter personal information to create an electronic profile before being allowed to accept the reciprocal invitation. Instead, the seed physician 39 merely has to log into the network, retrieve the invitation management interface 61 of FIG. 3, and electronically select the reciprocal invitation from the invitee. Upon making the electronic selection, the seed physician 39 is presented with the response interface 75 appearing in FIG. 4, which is generated by computer-readable logic and allows the seed physician 39 to accept, decline, or accept and extend yet another reciprocal invitation back to the invitee.

The option to only accept the invitation extended to the invitee 79 (FIG. 4) allows the invitee to accept the invitation and become a member of the seed physician's PCN without extending a reciprocal invitation in return. Again, accepting the invitation from the seed physician 39 establishes the invitee as a first-degree contact in the seed physician's PCN, and an electronic record of said relationship is recorded on a computer-readable medium of the system. The fact that the invitee has accepted the invitation to become a first-degree contact of the seed physician does not necessarily mean that the invitee has become a first-degree contact of the invitee. Whether the seed physician becomes a first-degree contact of the invitee is a consequence of the direction of the communication link. For example, in the scenario where the invitee accepts the seed physician's invitation and declines to offer a reciprocal invitation to the seed physician, the communication link is said to be unidirectional from the seed physician to the invitee. In this case, the invitee is a first-degree contact of the seed physician, but the seed physician is not a first-degree contact of the invitee. Further, details concerning the relationship of the invitee relative to the seed physician 39 may also be recorded on the computer-readable medium to indicate the invitee's "closeness" to, or "separation" from the seed physician 39 as described below.

Another option available to the invitee via the response interface 75 is to decline the invitation 81. If this option is selected by the invitee, the invitee will not become a first-degree contact of the seed physician, and no reciprocal invitation will be sent to the seed physician 39. Optionally, selection of this option can result in an electronic response in the form of e-mail or other electronic communication being transmitted to the seed physician 39 who extended the invitation. The electronic response can use a canned statement that politely and respectfully declines the seed physician's invitation. The invitee's response can optionally include a personal statement issued by the invitee indicating his/her reason for declining the invitation.

Once the invitee has selected the radio button (or other selection indicator) adjacent to the desired option, the "Commit Selection" button 84 can be electronically selected to initiate execution of computer-readable logic that will carry out the desired action. For instance, suppose the invitee selects the radio button adjacent to the accept invitation and send reciprocal invitation option 77 and then electronically selects the "Commit Selection" button 84. This causes the system to record the membership of the invitee in the seed physician's PCN and the relative position of the invitec in the social network relative to the seed physician 39 as described below.

The invitation-and-acceptance process of -rowing the social network and each social-network member's PCN can be continuously performed, and accordingly, the relationships of each social-network member to other social-network members may change over time. The seed physician 39 described above is among the one or more initial databases established as members of the social network by a network administrator to commence growth of the social network. However, it should be noted that extending invitations to join a PCN may not be limited to invitations from a seed physician 39 to an invitee who is not already a member of the social network. Instead, an invitation can be extended from any social-network member to any qualified non-member invitee (described above), to any other social-network member, or a combination thereof If, upon receiving an invitation from the seed physician 39 the invitee is not already a member of the social network, the invitee will become a member of both the social network and the seed physician's own PCN if the invitation is accepted. If, a first social-network member receives an invitation from a second social-network member, then the first social-network member becomes a member of the second social-network member's PCN (assuming the invitation is accepted), and the relationship between the two social-network members can be changed from their relationship prior to the invitation.

Any member of the social network can extend an invitation to join that member's PCN to any authorized entity, regardless of whether authorized entity is a member of the social network. For example, if the first social-network member was not in any way related to the second social-network member, or, if the first social-network member was separated by three degrees from the second social-network member before the invitation was accepted, once the invitation is accepted, the first social-network member becomes a direct contact of the second social-network member.

According to an alternate embodiment, in addition to being invited into a personal communication network, an authorized entity can optionally elect to register as the start (or seed) of a new PCN that will initially only include that entity. Before the entity is permitted to register as a new PCN member, however, a verification process is to be conducted to ensure that the entity attempting to register is actually interested or involved in the field of interest of the social network that the entity is seeking to join. For example, a physician may be verified to be board-certified and duly authorized to practice medicine. According to this physician example, to initiate a new PCN, and therefore become a physician within the medical social network, the user can enter an appropriate URL into an address line of a web-browser displayed by a remote computer terminal in a known manner. Upon accessing the system for the first time, computer-readable logic causes a new-user-registration interface analogous to registration-interface webpage described above to be displayed to the entity, which in this example is a physician. To minimize the number of unauthorized users that can use the system, physicians can register by creating a profile of themselves before they are able to log in and conduct a search or take advantage of other features of the system. The information entered by the user can be used to confirm the user's status as a licensed physician or other authorized user of the system. Returning users that have already completed their profile can log directly into the application, bypassing the initial registration process.

Figure 5:
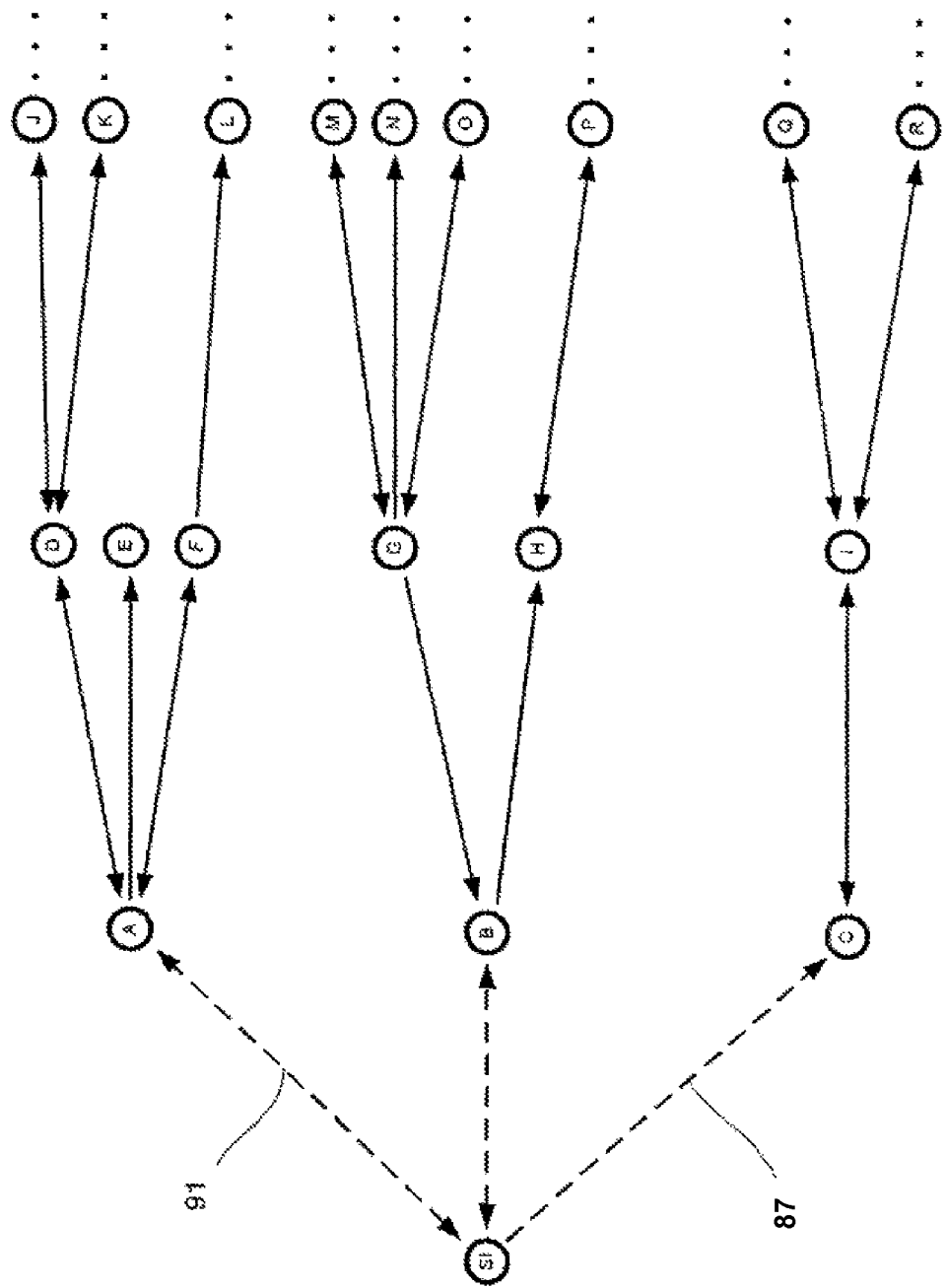
FIG. 5 is a schematic illustration of a PCN of a search initiator, who is himself a database in the social network.

Up to this point, reference has been made to the relationship or relative "closeness" or "separation" of social-network members relative to each other. When an invitee physician, whether a social-network member or not, accepts an invitation to join the PCN of social-network member (i.e., a member physician), a direct communication link is recorded on a computer-readable medium according to instructions in the computer-readable logic. If the invitee physician does not extend a reciprocal invitation back to the member physician, then the electronic record of the direct communication link indicates that the link is unidirectional, and that the invitation was extended from the member physician to the invitee physician. This arrangement is shown in FIG. 5, which illustrates an exemplary structure of a PCN, said PCN being that of a social-network member referred to as a search initiator. Each circle in FIG. 5 represents a physician who is a social-network member, and each line with terminal arrows represents a communication link between two social-network members. As previously mentioned, the communication links are electronic records that indicate the existence and direction of a previously-accepted invitation.

A unidirectional, direct communication link 87 is shown extending between the search initiator and invitee physician C. The communication link 87 is direct because there are no social-network members disposed between the search initiator and physician C, meaning that the search initiator has previously extended an invitation to join the search initiator's PCN directly to physician C and physician C accepted. The communication link 87 is unidirectional because either physician C chose not to extend an invitation (reciprocal or new) to the search initiator, or because the search initiator declined to accept an invitation from physician C to join physician C's PCN. Accordingly, the unidirectional nature of the communication link 87 is illustrated in the drawings by a line having only a single arrow at one of the two terminal ends. Upon accepting an invitation, the invitee physician becomes a member of the social network in general, and what will be referred to herein as a direct or first-degree contact of the member physician who originally extended the invitation. A first-degree contact, or direct contact, of a network member is a database that has accepted an invitation from the network member to join the network member's PCN. Thus, the first-degree contact is a database that the network member personally knows, or at least has personal knowledge of. Then, the invitee physician who accepts the invitation is said to be separated from the member physician who extended the invitation by one degree of separation. Direct communication links such as communication link 87 are indicated in the drawings by a dashed line. From the electronic record of the communication link, it can be deduced that the flow of information is from the member physician adjacent to the arrow end of the communication links shown in the drawings to the member physician at the opposite end of the communication link. In the example above, it is perceived that the flow of information is from physician C to the search initiator.

When a physician, whether a social-network member or non-social-network member, receives an invitation from a social-network member to join the PCN of that social-network member, the physician receiving the invitation can optionally extend a reciprocal invitation back to the physician who originally sent the invitation. If both the original and reciprocal invitations are accepted, then the direct communication link established and recorded according to instructions in the computer-executable logic of the between the two physicians is said to be bidirectional. In this instance, each physician becomes a first-degree contact of the other, and each physician is said to be separated from the other by one degree of separation.

Referring once again to FIG. 5, a direct, bidirectional communication link 91 has been established between the search initiator and physician A, and recorded on the computer-readable medium of the system. For such an arrangement, it can be deduced that the search initiator consults with physician A and physician A consults with the search initiator. Also, one or more communication links extending between social-network members can be dedicated to a particular topic. Thus, for example, the communication link 87 between the search initiator and physician C can be dedicated to the topic of research. This would be the case if the search initiator selected the topic "cancer" from the menu 48 when extending the invitation to physician C using the new-invitation interface of FIG. 2. Then, the electronic record of the communication link's existence also includes electronic data identifying the topic of the communication link.

As the social network grows, a physician who is a member of the social network will undoubtedly want to establish a direct communication link with one or more other physicians who are also already member(s) of the social network, and maybe even a distant member of the physician's own PCN. For example, this may be the case when one member physician learns that one of his or her trusted colleagues is already a member of the social network. The invitation-and-acceptance process facilitated by the computer-executable logic can be repeated, with a first member physician extending an invitation to a second member physician. If the invitation is accepted, a direct communication link is established and recorded along with its directionality according to instructions within the computer-executable logic. The directionality of the direct communication link in this case indicates that the invitation was extended by the first member physician and accepted by the second member physician, making the second member physician a first degree contact of the first member physician, or, in other words, the second member physician becomes separated from the first member physician by one degree of separation.

The PCN of a social-network member can comprise more than just the direct contacts of that social-network member. A first-degree contact of one the social-network member's first-degree contact would be considered to be two-degrees away, or in other words, separated by two degrees of separation. For instance, the direct contacts of the search initiator in FIG. 5 include physicians A, B and C since each is directly linked to the search initiator by a direct communication link having an arrow adjacent to at least each of the direct contacts (i.e., physicians A, B and C). Physicians D, E and F are each considered to be a second-degree contact of the search initiator since each are a direct contact of physician A, and the communication link between physician A and physicians D, E and F includes an arrow pointing in the direction of physicians D, E and F. Likewise, physician H is also a second-degree contact of the search initiator through physician B since physician B is a first-degree contact of the search initiator and physician H is a first-degree contact of physician B. The communication link between physician B and physician H in FIG. 5 includes an arrow pointing in the direction of physician H, which is indicative that physician B consults with physician H regarding some topic.

It should be noted, however, that physician G is not a second-degree contact of the search initiator (or a direct contact of physician B). This is because the communication link between physician B and physician G is unidirectional in the direction of physician B, and not in the direction of physician G. This indicates that physician G consults with physician B with regard to some topic, but it does not indicate that physician B consults with physician G. Hence, physician G is not considered a second-degree contact of the search initiator according to this embodiment.

In other examples any social-network member that can be reached by tracing any communication link, regardless of its directionality, to that social-network member is considered an indirect contact. For example, physician G may be considered a second-degree contact of the search initiator in FIG. 5 according to these embodiments. The communication link between the search initiator and physician B, followed by the communication link between physicians B and G could be followed in order to reach physician G starting at the search initiator. These embodiments merely require a continuous chain of communication links to connect two social-network members for those members to be considered direct or indirect contacts.

A chain of communication is a communication path that has an uninterrupted path of communication links from one database to another. In some examples, all communication links in the chain of communication may be dedicated to at least one common topic or context. For instance, one example may require all communication links in a chain of communication extending between two databases in a PCN to be related in some manner to "cancer," or another medical topic. The context of the communication links in a chain of communication can be defined by a search initiator as described below.

The number of degrees of separation between a social-network member and another database in the social-network member's PCN can be more than two. A social-network member can have third-degree contacts, fourth-degree contacts, fifth-degree contacts, . . . and $n^{th}$-degree contacts, where n can be any positive integer. Just as for the second-degree contacts, a third-degree contact is a member of the social-network member's PCN that is separated from the social-network member by three communication links connecting two intervening contacts. For illustrative purposes, physician J in FIG. 5 would be considered to be a third-degree contact of the search initiator since physician J is separated from the search initiator by two intervening social-network members, physicians A and D. And again, some examples may require the directionality of each communication link within the chain of communication between the search initiator and the $n^{th}$-degree contact to point in the direction away from the search initiator, while other examples may require a continuous chain of communication to join all relevant social-network members, regardless of directionality.

Thus, the search initiator's PCN comprises that portion of the social network made up of physician(s), other types of database(s), and any combination thereof that are directly, indirectly, or both directly and indirectly linked to the search initiator. The term "search initiator" is merely used herein to denote a social-network member who can access the system to search for other social network members who are likely to possess information about a topic of interest. It should be understood, however, that any social network member can be a search initiator.

The search initiator can limit the population of his or her PCN that is eligible to be displayed as a search result to a subset of the PCN that is separated from the search initiator within a maximum number of degrees of separation. The subset can be limited by the search initiator as desired to include only those databases that are directly, indirectly, or both directly and indirectly linked to the search initiator within m degrees of separation, wherein m is any positive integer, or the subset can be unbounded to include the search initiator's entire PCN. Thus, if m=2, for example, the PCN subset comprises all physicians that are directly, indirectly, or both directly and indirectly linked to the search initiator and are separated from the search initiator by two or fewer degrees of separation. And for embodiments that merely require the existence of a communication link, regardless of directionality, to connect two social-network members, this would include physicians A-I, inclusive, since those physicians are separated from the search initiator by two or less degrees of separation. But for embodiments requiring the directionality of each communication link to point away from the search initiator, this would only include physicians A-F, H and I.

Formation of the social network and PCNs in this manner allows for a search method to identify databases likely to possess information about a particular topic. Each of the first-degree contacts of the search initiator separates the search initiator from contacts that are further separated from the search initiator. It can be deduced that the search initiator trusts the first degree contact, otherwise the search initiator would not have extended an invitation to the first-degree contact to join the search initiator's PCN. It follows that the search initiator can make a preliminary determination about the trustworthiness and likelihood of the second-degree contact to possess useful information by considering the intervening first-degree contact. For example, suppose that a first-degree contact of the search initiator is a physician in a teaching hospital who is primarily concerned with academic research on cancer. The search initiator can surmise that the contacts directly and indirectly linked to this first-degree contact are likely to have a similar background. Thus, in circumstances when the search initiator is seeking information about cancer research, the search initiator is likely to desire to limit the scope of a search for said cancer information to those social-network members that are directly and indirectly linked to the first-degree contact.

In another example, the first-degree contact may have become less reputable in light of recent accusations of falsifying experimental data. If a second-degree contact of the search initiator that is directly linked to the first-degree contact was at one time a research partner with the first-degree contact, the search initiator can exercise caution in consulting with the second-degree contact. Regardless of the search initiator's relationship with the first-degree contact, the search initiator can often obtain an initial impression about the knowledge and other attributes of the second-degree and further separated contacts based on the search initiator's familiarity with the first-degree contact that separates them.

Accordingly, some examples may provide a search initiator with the ability to search at least a portion of the social network for information pertaining to a topic. Just as before, the term "search initiator" is used hereinafter and in the figures to refer to a physician who is a member of the social network and is using the system to initiate a search of at least a portion of the social network in an attempt to locate information about a topic.

Figure 6:
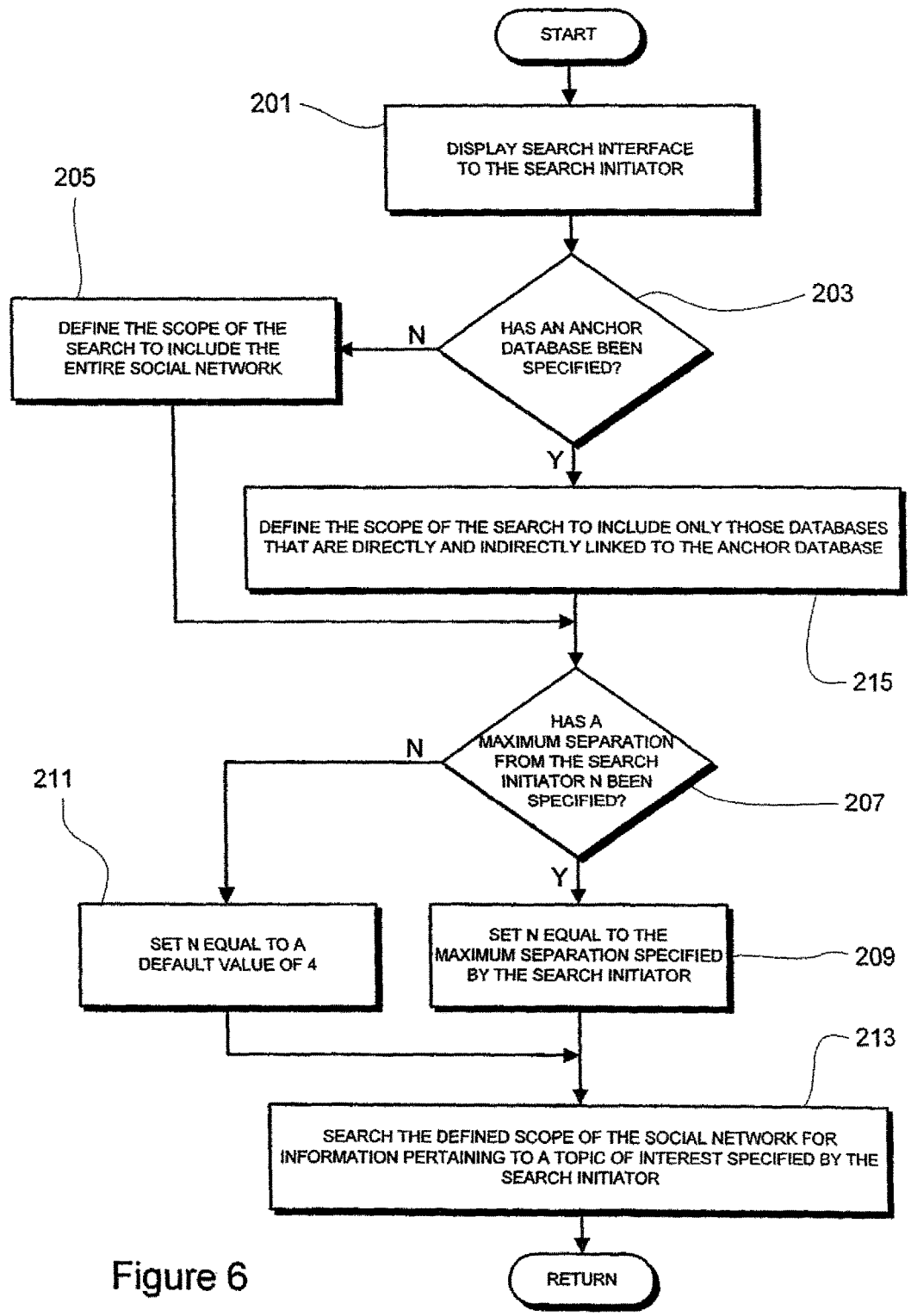
FIG. 6 is a flow diagram illustrating steps of a method according to an embodiment of the present invention.
Figure 7:
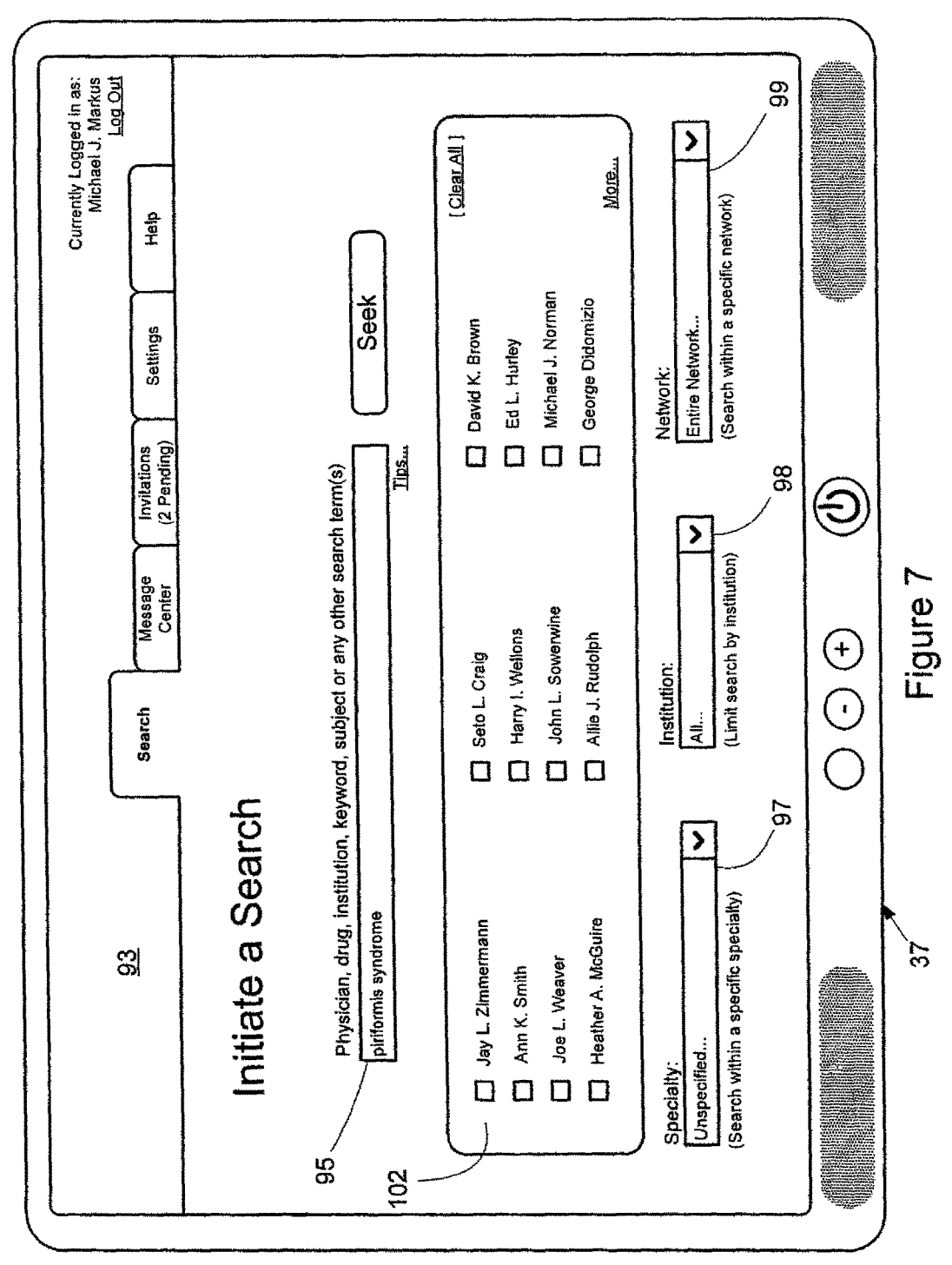

FIG. 6 is a flow diagram illustrating an example method for searching a collection of databases The search interface 93 shown in FIG. 7 is displayed at step 201 to provide a front end visible to the search initiator that includes input fields to allow the search initiator to specify the search criteria. As shown in FIG. 7, the search interface 93 provides the search initiator with a search-string field 95 in which the search initiator can enter a search string in an attempt to limit the scope of the search to information pertaining to the topic about which the search initiator is inquiring. The phrase "piriformis syndrome" is illustrated as the search string for this embodiment.

Other search-narrowing criteria can also be presented to the search initiator in the search interface screen 93. The goal of providing the search initiator with such search-narrowing criteria is to minimize the number of irrelevant search results returned by the search. Examples of search-narrowing criteria include a medical specialty 97 any search results must satisfy, an institution at which any search results practice 98, a network designator 99 for specifying a network such as the cancer network, and so on. The search results to be returned include those databases that are likely to possess information sought after by the search initiator, as defined by the search string, anchor database, search-narrowing criteria, or any combination thereof Further, the search interface 93 can provide the search initiator with a plurality of search strategies that control the extent of the social network to be searched for databases possessing the information being sought. Examples of different search strategies include a broadcast search and a directed search. Which of the search strategies being pursued is determined at step 203 in the flow diagram of FIG. 6. If the search initiator selects an anchor database from the menu 102 of the search initiator's first-degree contacts, then a directed search is to be conducted. An anchor database is a first-degree contact of the search initiator that the search initiator believes is likely to possess the sought-after information, or is likely to be directly or indirectly linked to a database that is likely to possess the sought-after information. In other words, the search initiator believes that the anchor database is a first-degree contact who is likely to possess information about the search criteria, likely possesses a database in his PCN that is likely to possess information about the search criteria, or a combination thereof. If, on the other hand, no anchor database is selected from the menu 102, then a broadcast search is to be conducted.

According to one embodiment, a broadcast search includes an electronic search according to the search criteria that permeates through the population of the entire social network, the search initiator's PCN, or both as defined at step 205 for databases likely to possess sought-after information. For a broadcast search, the search initiator can enter a search string into the search-string field 95 and any other search-narrowing criteria 97, 98, 99 to further focus the search for the information. The search string will commonly be a word or phrase that is likely to be closely related to information found in an electronic social-network profile belonging to a social-network member who, among all members of the social network is likely to possess the desired information about the topic of interest. The electronic profile of each social-network member is searched for information that is closely related to the search string and other search-narrowing criteria. Such an electronic search can utilize any conventional search technology such as metadata searching, word searching, and the like to conduct the search of the electronic profiles of the social-network members for information relating to the search string. Computer-executable instructions can control searching of the electronic records representing databases in the social network to find matches to a query and rank them in an order of relevance.

Search results returned by the search as being likely to possess information about the search string are also compared to the direct and indirect contacts of the search initiator. The final search results to be displayed include those that both satisfy the search string and any additional search criteria, and are linked directly, indirectly, or both directly and indirectly to the search initiator. The maximum allowable degrees of separation between the search initiator and the search results eligible to be displayed can optionally be defined by the search initiator since a strong inference is difficult to make about the reliability of physicians separated from the search initiator by a large number of intervening physicians. Alternately, the maximum allowable degrees of separation between the search initiator and the search results eligible to be displayed can be set to a default value by the system. Although the search initiator can limit the maximum degree of separation of search results to be displayed, the search can still permeate throughout the entire population of the social network, the search initiator's PCN, or both. This limitation is merely a limit of the number of search results to be displayed and not a limit on the number of databases to be searched. Alternate embodiments, however, may limit the population to be searched to coincide with the number of search results to be displayed. Thus, if it is determined at step 207 that the maximum allowable degrees of separation for displayed results has been defined by the search initiator, then the search results displayed to the search initiator will be limited to that value at step 209. However, if it is determined at step 207 that no value has been specified, then a default value of 4 can be established at step 211 to limit the maximum allowable degrees of separation between the search initiator and databases to be displayed as search results for practical purposes.

Other embodiments can leave the maximum allowable degrees of separation unbounded if not specified at step 207 and display all returned results. According to such embodiments, any database that is returned by the search is to be displayed. The search initiator can view a large number of results by manipulating a scroll bar or other navigation tool displayed by the display device used to display search results in a known manner to bring out-of-sight search results into view of the search initiator.

Other examples may include determining that a broadcast search is to be conducted at step 203 if all first-degree contacts in menu 102 of the search initiator are selected as anchor databases. For these embodiments, the scope of the search is limited to the entire PCN of the search initiator. This accomplishes the same result as conducting a search of the entire social-network population and only displaying those results that are directly or indirectly linked to the search initiator. Essentially, the scope of the search in either case is limited to the entire PCN of the search initiator.

Once the search string and any other desired search criteria have been established, the search initiator can electronically select the "Seek" button 105 to begin execution of computer-readable logic for controlling the broadcast search. Once the "Seek" button 105 has been selected, computer-readable logic initiates the broadcast search at step 213 for databases that are likely to possess information about the search string and that satisfy any other search criteria.

Figure 8:
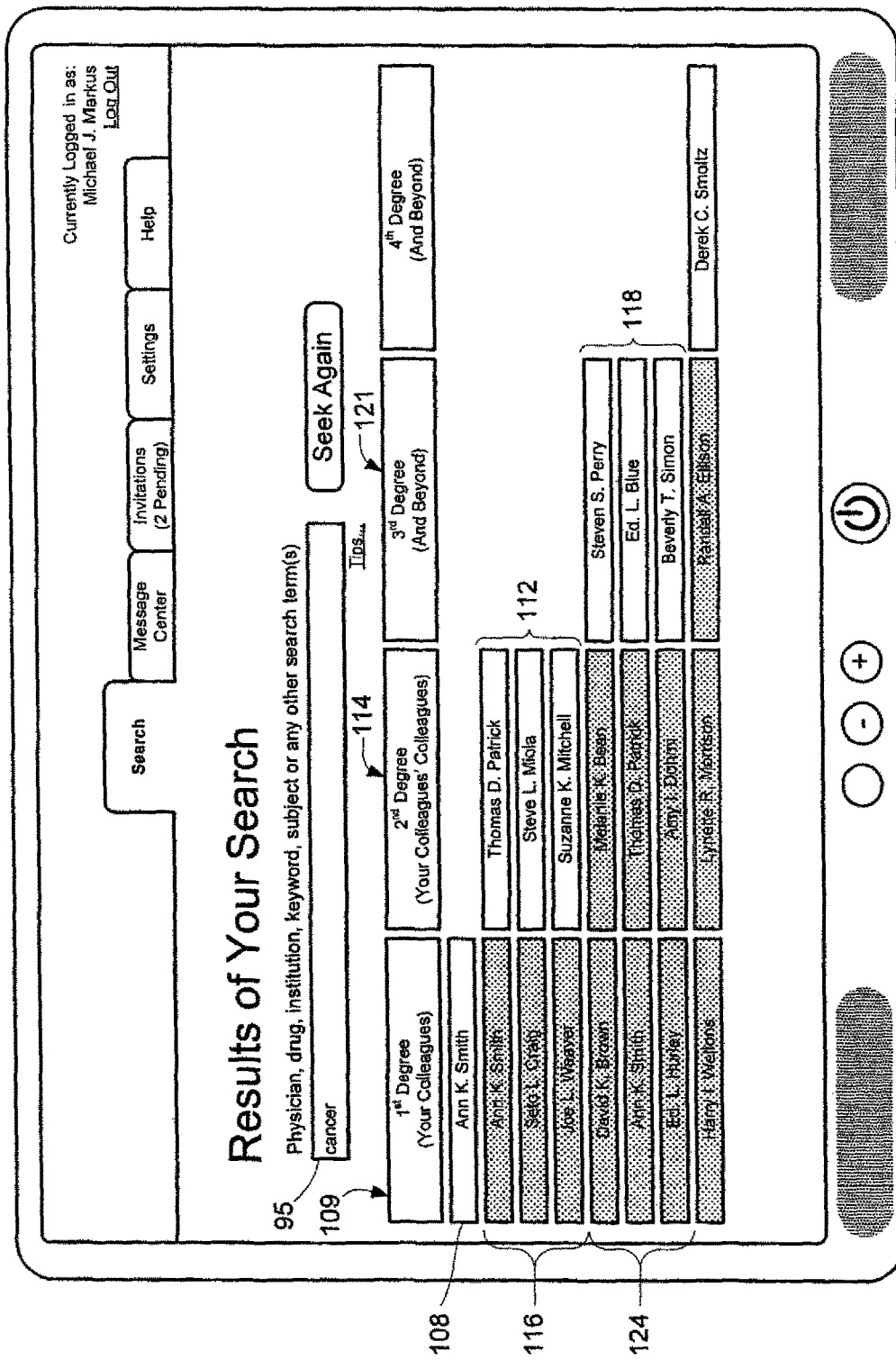
FIG. 8 is an illustrative depiction of a search-results interface displayed by a display device to present the results of a broadcast search to a search initiator.

FIG. 8 is an illustrative display of search results returned by a broadcast search. The search results are to be displayed in a manner that conveys relative of separation of the search result from the search initiator, and may also be grouped according to the number of degrees separating each search result from the search initiator. For example, the search string that returned the search results shown in FIG. 8 was "cancer," which is listed in the search-string field 95. The first-degree, or direct contacts of this particular search initiator (which is Mike Markus, as shown in the upper night corner of FIG. 8) that are likely to possess information pertaining to cancer include those in the highlighted region 108 in the first column 109, which is labeled "1st Degree (Your Colleagues)." Likewise, those members of the search initiator's PCN who are separated from the search initiator by two degrees of separation and are likely to possess information on cancer are located in the highlighted region 112 of the second column 114, labeled "2nd Degree (Your Colleagues' Colleagues)." These second-degree contacts are located adjacent to first-degree contacts in a non-highlighted region 116 of the first column 109. The first-degree contacts in this non-highlighted region 116 of the first column 109 are intervening contacts, also referred to as intervening nodes and intervening databases, disposed between the search initiator and the second-degree contacts in the region 112 who were returned as search results.

This method of returning search results can continue out to the desired maximum number of degrees of separation to be displayed as search results that was specified by the search initiator, or to the default value in the absence of a search-initiator defined value. Thus, third-degree contacts in the highlighted region 118 of the third column 121 labeled "$3^{rd}$ Degree (And Beyond)" are separated from the search initiator by two intervening contacts, which are first and second degree contacts of the search initiator located in the non-highlighted region 124 of the first and second columns 109, 114, respectively.

As can be seen from FIG. 8, many different first-degree contacts of the search initiator are listed in the $1^{st}$-degree contact column 109 as intervening contacts between the search initiator and various search results. The many different $1^{st}$-degree contacts listed in the $1^{st}$-degree contact column 109 is a result of the broadcast search because an anchor database was not selected by the search initiator to limit the $1^{st}$-degree contacts who could be returned as an intervening contact.

In contrast, a directed search strategy limits the population of the search initiator's PCN that can be returned by a search and displayed to the search initiator. A directed search limits the databases in the search initiator's PCN that are eligible to be displayed as search results to those contacts within a portion of the search initiator's PCN that is less than the search initiator's full PCN. Referring once again to FIG. 6, if it is determined at step 203 that the search initiator has selected one or more, but less than all of his first-degree contacts as an anchor database from the menu 102 (FIG. 9), then the directed search strategy is to be conducted. Selecting an anchor database limits the population of the search initiator's PCN that can be returned as search results at step 215 to those who are directly, indirectly, or both directly and indirectly linked to the anchor database(s) selected by the search initiator. When conducting a directed search, the search initiator selects the one or more of his first-degree contacts from the menu 102 who the search initiator initially believes possesses the desired information, or is likely to have a database in his PCN that is likely to possess the sought-after information. Each first-degree contact selected from the menu 102 by the search initiator to limit the scope of the directed search is called an anchor database.

Figure 9:
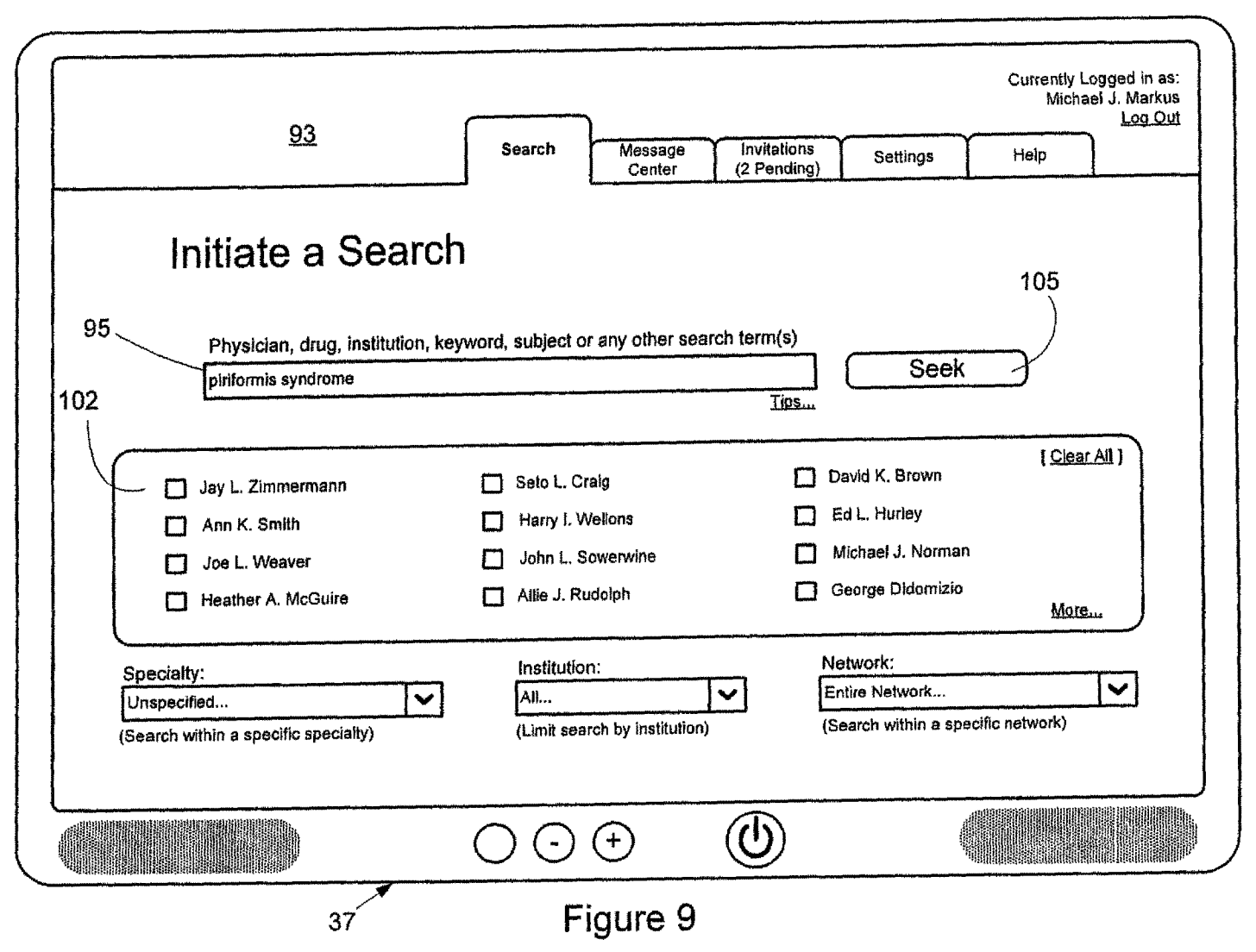

In general, selection of an anchor database from amongst a search initiator's first-degree contacts requires any search results that are to be displayed to the search initiator to be directly, indirectly, or both directly and indirectly linked to the anchor database. In FIG. 9, the first-degree contacts "Ann K. Smith," "Seto L. Craig" and "David K. Brown" have been selected as anchor databases by the search initiator from menu 102 in the search interface 93. Each selection is made by electronically checking the check box adjacent to each first-degree contact to be specified as an anchor database. The scope of the directed search of the social network for members who could possibly possess information on the topic of "cancer," which is specified in the search-string field 95, can optionally encompass the entire social network. Alternately, the scope of the directed search of the social network for members who could possibly possess information on the topic of "cancer" can be limited to only those social-network members that are directly, indirectly, or both directly and indirectly linked to an anchor database. But, regardless of the portion of the social network searched during the directed search, only those search results returned by the search as satisfying the search string and any other specified search criteria and that are directly, indirectly, or both directly and indirectly linked to an anchor database are to be displayed to the search initiator as directed search results, as shown at step 215 (FIG. 6).

Just as with the broadcast search, the method may further include determining whether the search initiator has specified a maximum allowable degree of separation to be displayed as search results at step 207. The search initiator may not be required to specify such a value, and if the search initiator elects not to, then a default value is set as the maximum allowable degrees of separation to be displayed. The default value in FIG. 6 is 4, however, default values may also be included, which can be any positive integer, or unbounded altogether. An unbounded default value will cause all search results that (1) are directly, indirectly, or both directly and indirectly linked to the anchor database; and (2) satisfy the search criteria are to be displayed along with any intervening contacts, regardless of how far removed the search results are from the search initiator.

If however, the search initiator has elected to specify a maximum allowable degree of separation to be displayed at step 207, then this value is set as the maximum degrees of separation that can separate the search initiator from a directed search result to be displayed at step 209. If the maximum degree of separation is bounded, then all search results that (1) are directly, indirectly, or both directly and indirectly linked to an anchor database; (2) satisfy the search criteria; and (3) are within the maximum allowable degrees of separation are to be displayed along with any intervening contacts between the search initiator and each search result.

Once the search string and any other search criteria have been established, and an anchor database has been selected, the search initiator can electronically select the "Seek" button 105 (FIG. 9) to begin execution of computer-readable logic for controlling the directed search. Once the "Seek" button 105 has been selected, computer-readable logic initiates the directed search at step 213 for databases that: (1) are likely to possess information about the search string and that satisfy any other search criteria, and (2) are directly, indirectly, or both directly and indirectly linked to the anchor database. Of the databases returned by the directed search, the results to be displayed can further be limited to those within the maximum degree of separation as specified by the search initiator at step 209 or as set by default at step 211.

In another example, once the directed search has been initiated, the computer-readable logic controls the searching of the electronic profile of each anchor database selected by the search initiator. The search of each anchor database is conducted to identify whether the anchor database is likely to possess the information being sought by the search initiator. The directed search proceeds to search the PCN of each anchor database selected by the search initiator to identify which, if any, databases in the PCN of each anchor database is likely to possess the sought-after information related to the search string.

According to another example, the directed search can include a search of the electronic profile of each member of the entire social network. According to such embodiments, the search results are then filtered such that the search results that are to be returned and displayed to the search initiator are those that (1) bear some relationship to the search string and satisfy any other criteria, and (2) are directly, indirectly, or directly, indirectly or both directly and indirectly linked to an anchor database.

Figure 10:
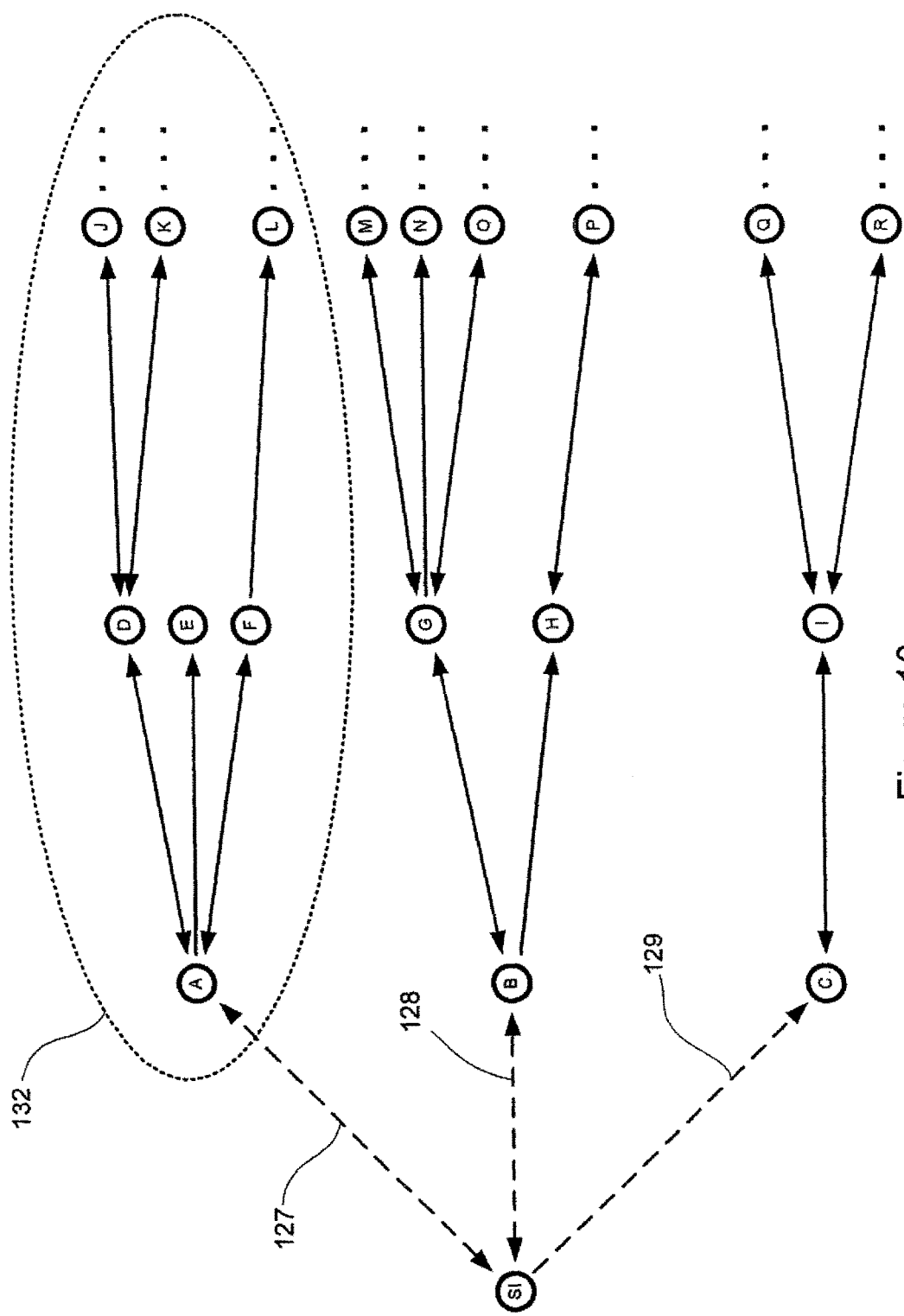
FIG. 10 is a schematic illustration of a PCN of a search initiator, wherein a portion of the PCN including databases that are eligible to be displayed as results of a directed search is identified.

However, there are instances when the search initiator himself is a first-degree contact of the anchor database, such as when a bidirectional link 127 exists between the search initiator and physician A as the anchor database in FIG. 10. In such cases, the search of the anchor database's PCN is conducted by disregarding the directionality of the communication link 127 that points toward the search initiator. Doing so prevents search results from a search of the entire PCN of the search initiator from being returned and displayed to the search initiator, as would occur for a broadcast search.

FIG. 10 illustrates a simple example of how a directed search of the search initiator's PCN can be conducted. Relative to the search initiator, physicians A-C are the search initiator's first-degree contacts, as indicated by the broken lines 127, 128 and 129 between the search initiator and each of physicians A-C, respectively. Likewise, physicians D-I are second-degree contacts of the search initiator, while physicians J-R are third-degree contacts. The search initiator's PCN can extend much further, but said extension is represented generally by the ellipses " . . . ". If the search string is "cancer" and physician A is selected as the anchor database by the search initiator, then the portion of the search initiator's PCN that is searched by a directed search conducted using these criteria is encircled by the dashed oval 132. All social-network members within the oval 132 are directly or indirectly linked to physician A. Neglecting the communication link extending from physician A to the search initiator prevents physician B from being included within the portion of the anchor database's PCN that is to be searched, since otherwise, physician B would be two degrees of freedom from the anchor database (physician A).

FIG. 10 illustrates a simple example of a PCN of the search initiator. The search initiator's PCN in FIG. 10 lacks communication links that extend between generally-parallel branches. Generally-parallel branches are the chains of contacts that extend away from the search initiator, each chain beginning with a first-degree contact of the search initiator. The portion of the search initiator's PCN enclosed by oval 132 is an example of a branch. As the social network develops over time, however, new communication links are established and the relationships amongst members of the social network, and even amongst members of a PCN can, and likely will change. For example, in FIG. 10, consider if the maximum number of degrees of separation between the search initiator and PCN members to be displayed as search results of a directed search was defined by the search initiator to be 3. Hence, by selecting physician A as the anchor database, the electronic profile of physicians J, K and L would be included in the directed search, and could be returned as search results.

Figure 11:
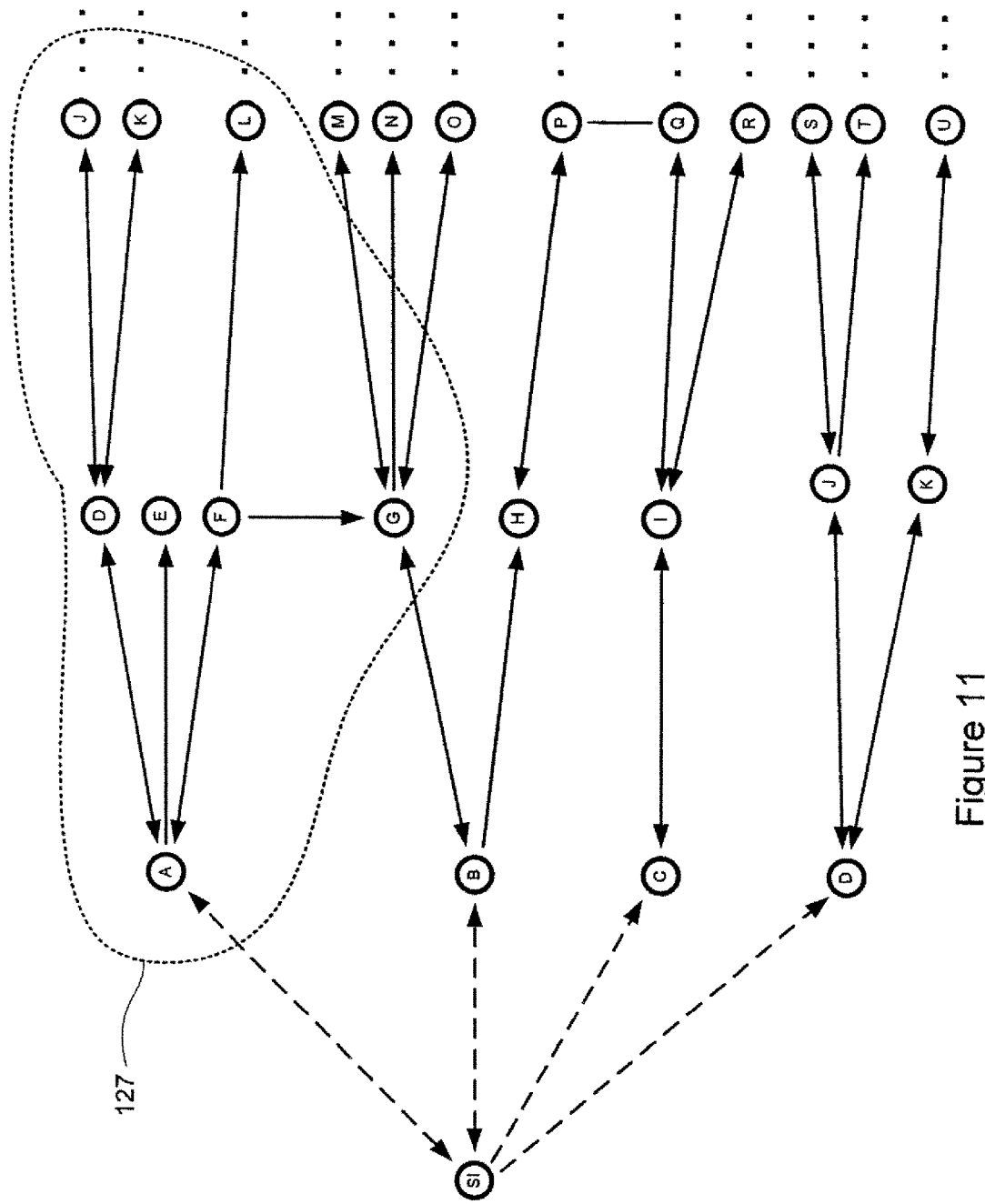
FIG. 11 is a schematic illustration of a PCN of a search initiator, wherein a portion of the PCN including databases that are eligible to be displayed as results of a directed search is identified.

In FIG. 11, however, it is shown that a unidirectional communication link has been established from physician F to physician G. Thus, physician G has accepted an invitation to join physician F's PUN, and has become a first-degree contact of physician F. Now, consider a directed search conducted with the maximum number of degrees of separation allowed between the search initiator and those physicians to be returned as search results displayed to the search initiator is again 3, and physician A is the anchor database. Those physicians who can be displayed to the search initiator as search results of a directed search, assuming they are likely to possess information about the search string and satisfy any other criteria, are enclosed by the dashed line 135. As can be seen, physician G in FIG. 11 has now been included within the group of potential search results of the directed search due to the communication link formed from physician F to physician G. Physician G is now within three degrees of separation from the search initiator.

Figure 12:
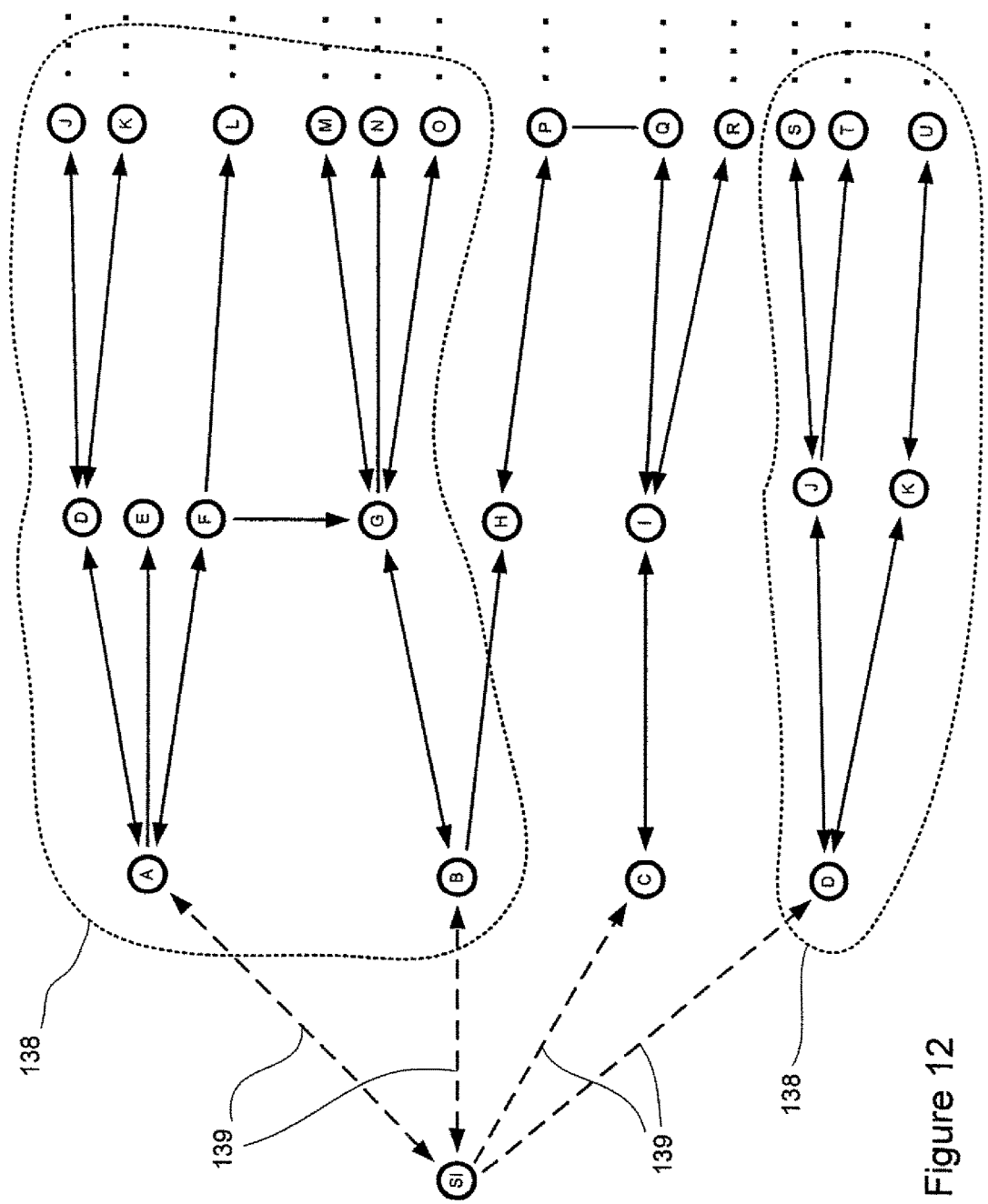
FIG. 12 is a schematic illustration of a PCN of a search initiator, wherein a portion of the PCN including databases that are eligible to be displayed as results of a directed search is identified.

FIG. 12 provides yet another illustration of an expanding portion of the search initiator's PCN that can include search results of a directed search, said portion being enclosed by dashed lines 138. The relationships between the members of the search initiator's PCN has not changed, nor has the selection of physician A as the anchor database, but the maximum allowable degrees of separation relative to the search initiator has been changed from 3 to 4. Now, in FIG. 12, the members of physician A's PCN that can be included in search results of the directed search to be displayed to the search initiator include physicians A, B, D-G, J-O and S-U. Physician D is a second-degree contact of the search initiator when looking down the branch of the search initiator's PCN beginning with the anchor database (Physician A), and thus, according to this example, physician D is eligible to be displayed as a search result of this directed search. This is true even though physician D is also a non-selected first-degree contact (i.e., not selected as an anchor database) of the search initiator. For any directed search, the degrees of separation separating a database from the search initiator is to be determined with regard to the database's relationship to the search initiator within the anchor database's PCN. For the example shown in FIG. 12, physician A is separated one degree from the search initiator, physicians D, E and F are separated by two degrees of separation, physicians G, J, K and L by three degrees, and physicians B, M, N, O, S, T and U by four degrees of separation. Accordingly, physicians S-U are also within the anchor database's PCN and are within 4 degrees of separation from the search initiator, and hence, they are included in that portion of the search initiator's PCN that includes databases eligible to be displayed as search results for this directed search. The same can be said of any first-degree contact(s) of physician L.

Considering the PCN structure of FIG. 12 where the maximum allowable degrees of separation of the PCN subset relative to the search initiator is 5, it should be noted that the communication links 139 between the search initiator and each of the search initiator's first degree contacts are disregarded for determining the population of the search initiator's PCN that includes databases eligible to be displayed as search results returned by a directed search. As previously mentioned, allowing the scope of the directed search to reach the search initiator would transform the directed search into a broadcast search. Thus, in FIG. 12 with the maximum allowable degrees of separation for inclusion in the PCN subset set to 5, the communication link 139 extending between physician B and the search initiator is ignored, and the search initiator is not considered to be five degrees separated from himself. The communication link 139 between physician A and the search initiator is also disregarded for purposes of identifying the search initiator's PCN subset that includes databases eligible to be displayed as search results of the directed search.

Figure 13:
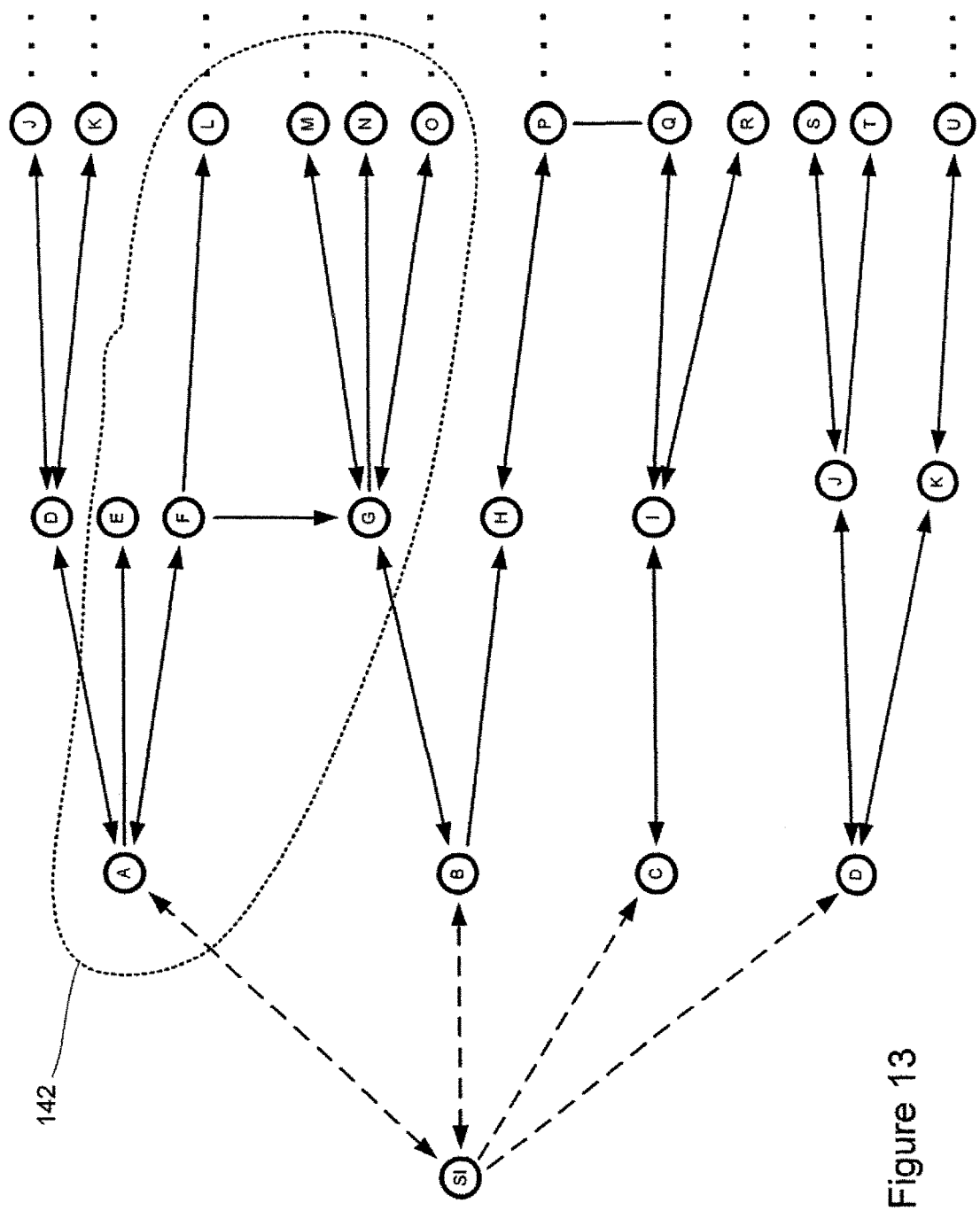
FIG. 13 is a schematic illustration of a PCN of a search initiator, wherein a portion of the PCN including databases that are eligible to be displayed as results of a directed search is identified.

According to another example, any first-degree contact of the search initiator that is not selected as an anchor database is excluded from the portion of the search initiator's PCN (referred to as the "eligible portion") that includes databases that are eligible to be displayed as search results of a directed search. Additionally, any "downstream" contacts of the non-selected first-degree contacts are also excluded from the population of the subset of the search initiator's PCN that are eligible to be displayed as search results of a directed search. To identify the downstream contacts of a non-selected first-degree contact that are excluded from the eligible subset of the search initiator's PCN in this example, refer to the schematic illustration of the search initiator's PCN in FIG. 13. The maximum allowable degrees of separation for the PCN subset including eligible databases has been set to 4 by the search initiator. To determine the eligible portion of the search initiator's PCN, analysis of the relationships amongst databases begins at each database that was selected as an anchor database, which in this example, is physician A. Just as before, all communication links from the search initiator's first-degree contacts leading back to the search initiator are ignored, and treated as if they didn't exist for this analysis. Physician A, as the anchor database, is one-degree from the search initiator, and since physician A was specified as the anchor database, physician A is within the eligible portion of the search initiator's PCN in this example. At the next level down the branch of the search initiator's PCN that begins with the anchor database are physicians D, E and F.

Physician D is a non-selected first-degree contact of the search initiator in the present example, and thus, physician D and physician D's contacts (in the example illustrated in FIG. 13, physicians J and K) that are further separated from the anchor database down the branch of the search initiator's PCN beginning with physician A are not included in the eligible portion of the search initiator's PCN. That is not to say that physicians J and K, and their contacts that are further separated from the anchor database (physician A) are necessarily excluded. Physicians J and K could each be included in the eligible portion of the search initiator's PCN if, for instance, they were first-degree contacts of physician L in FIG. 13. In this case, they would still be within the maximum allowable degrees of separation from the search initiator to fall within the eligible portion of the search initiator's PCN. But that does not appear to be the case in this example, and thus, physicians J and K are not included in the eligible portion of the search initiator's PCN.

The other physicians that are second-degree contacts of the search initiator and are within the branch of the search initiator's PCN beginning with the anchor database are physicians E and F. Since neither of these physicians are first-degree contacts that were not selected as an anchor database, and both physicians E and F are directly linked to the anchor database (and therefore are not "downstream" of a non-selected first-degree contact), both of them fall within the eligible portion of the search initiator's PCN that can be displayed as search results for the directed search.

Figure 13B:
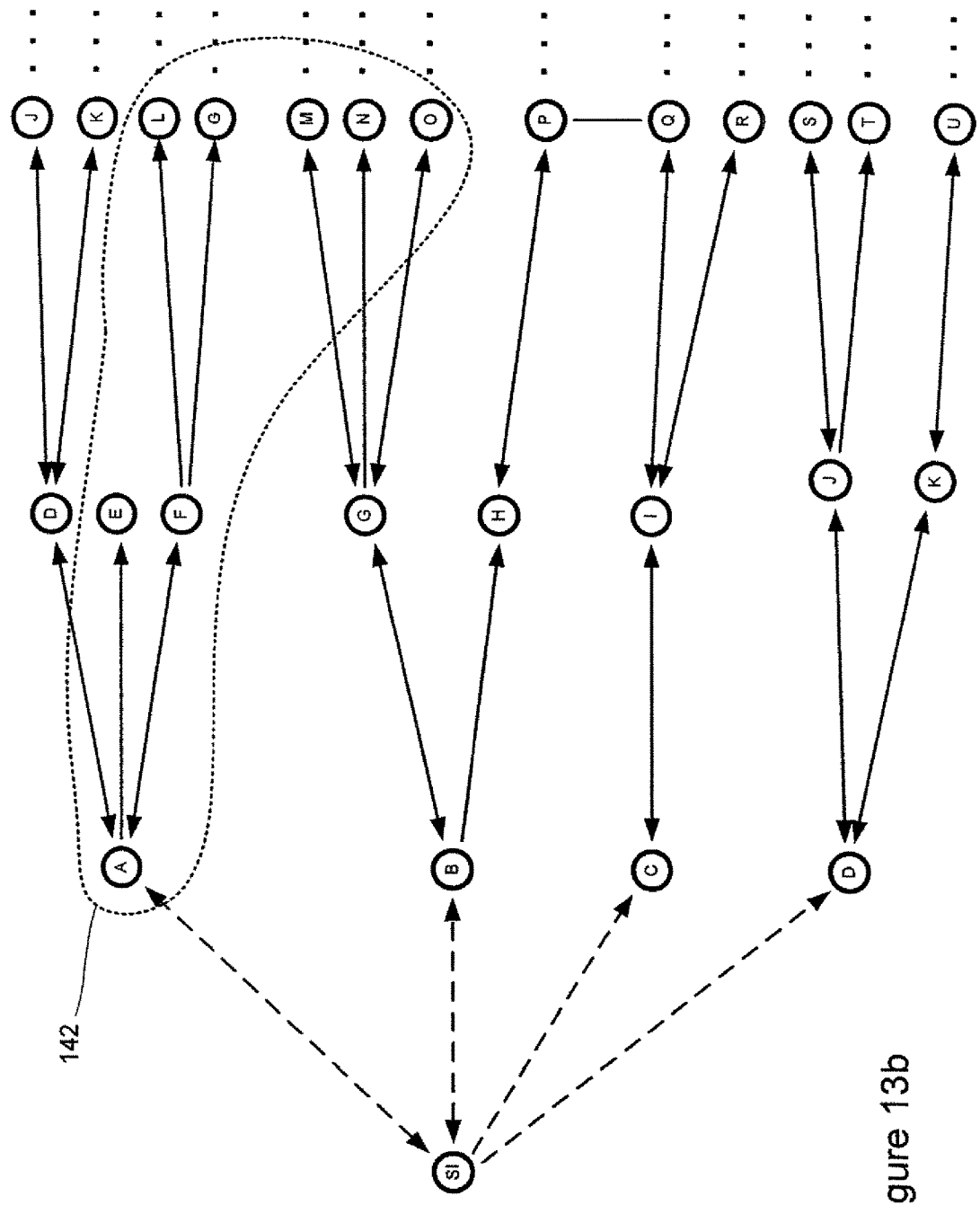
FIG. 13b is a redrawn, schematic illustration of the PCN shown in FIG. 13.

Continuing down the anchor database's branch to the first-degree contacts of physicians E and F (i.e., the third-degree contacts of the search initiator), the physicians to analyze are physicians L and G to determine if they fall within the eligible portion of the search initiator's PCN. To do this, it is helpful to redraw the search initiator's PCN to eliminate interaction between the branches beginning with physician's A and B, as was done in FIG. 13b. In FIG. 13b, the communication links extending from physician F to physician G has been redrawn such that physician G appears twice in FIG. 13b, once in the branch of the search initiator's PCN beginning with physician B, and once in the branch of the search initiator's PCN beginning with physician A. Both physician F and physician B still have a communication link extending to physician G, but each communication link falls entirely within its respective branch of the search initiator's PCN. When redrawn in this manner, it can be seen that both physician L and physician G fall within the eligible portion of the search initiator's PCN since they both fall within the maximum allowable degrees of separation and both fall within a branch of the search initiator's PCN that begins with the anchor database. And although physician G is a direct contact of a non-selected first-degree contact (physician B) of the search initiator, physician G is within the maximum allowable degrees of separation from the search initiator and is also a direct contact of a physician F, who falls within the eligible portion of the search initiator's PCN. This is unlike the case of physicians J and K discussed above, since physicians J and K each a direct, indirect, or both a direct and indirect contact of only a non-selected first-degree contact (physician D) of the search initiator (i.e., physicians J and K were members of a PCN of only a non-selected first-degree contact). Thus, physician G falls within the eligible portion of the search initiator's PCN as a $3^{rd}$-degree contact of the search initiator, even though physician G would otherwise be considered a $2^{nd}$-degree contact of the search initiator linked to physician B.

Since the maximum allowable degrees of separation from the search initiator is 4, each first-degree contact of physicians L, G, M, N and O that is not a first-degree contact of the search initiator would also fall within the eligible portion of the search initiator's PCN that could be displayed as search results of the directed search.

To summarize this example, any first-degree contact of the search initiator that is not selected as an anchor database is excluded from the eligible portion of the search initiator's PCN. Further, each database in the PCN of a non-selected first-degree contact that is not: (1) a direct contact of a database that falls within the eligible portion of the search initiator's PCN, and (2) within the maximum allowable degrees of separation from the search initiator (when observed down a branch beginning with an anchor database) is excluded from the eligible portion of the search initiator's PCN.

Another example can include computer-executable instructions that will exclude from the portion of the search initiator's PCN eligible to be displayed as search results of a directed search any first-degree contacts of the search initiator who were not selected as an anchor database. But in contrast to the previous example, such a non-selected anchor database can act as an intervening node that links the search initiator to a search result that is to be displayed to the search initiator. To illustrate this embodiment, assume in FIG. 14 that the maximum allowable degrees of separation relative to the search initiator is set to three, physician A is selected as an anchor database and physician D is not, and that both physicians D and J are likely to possess information about the search string and satisfy any other search criteria of a directed search based on their electronic profile information. The search results to be displayed by this particular directed search will exclude physician D as a non-selected first-degree contact but will include physician J, and will convey to the search initiator that the communication path between the search initiator and physician J includes physician D. This is true for this example even though physician D is within the maximum allowable degrees of separation from the search initiator and is within the branch of the search initiator's PCN beginning with physician A as the anchor database. The portion of the search initiator's PCN that is eligible to be returned and displayed as directed search results for this example is enclosed by the dashed lines 145 and 148 in FIG. 14.

Figure 14:
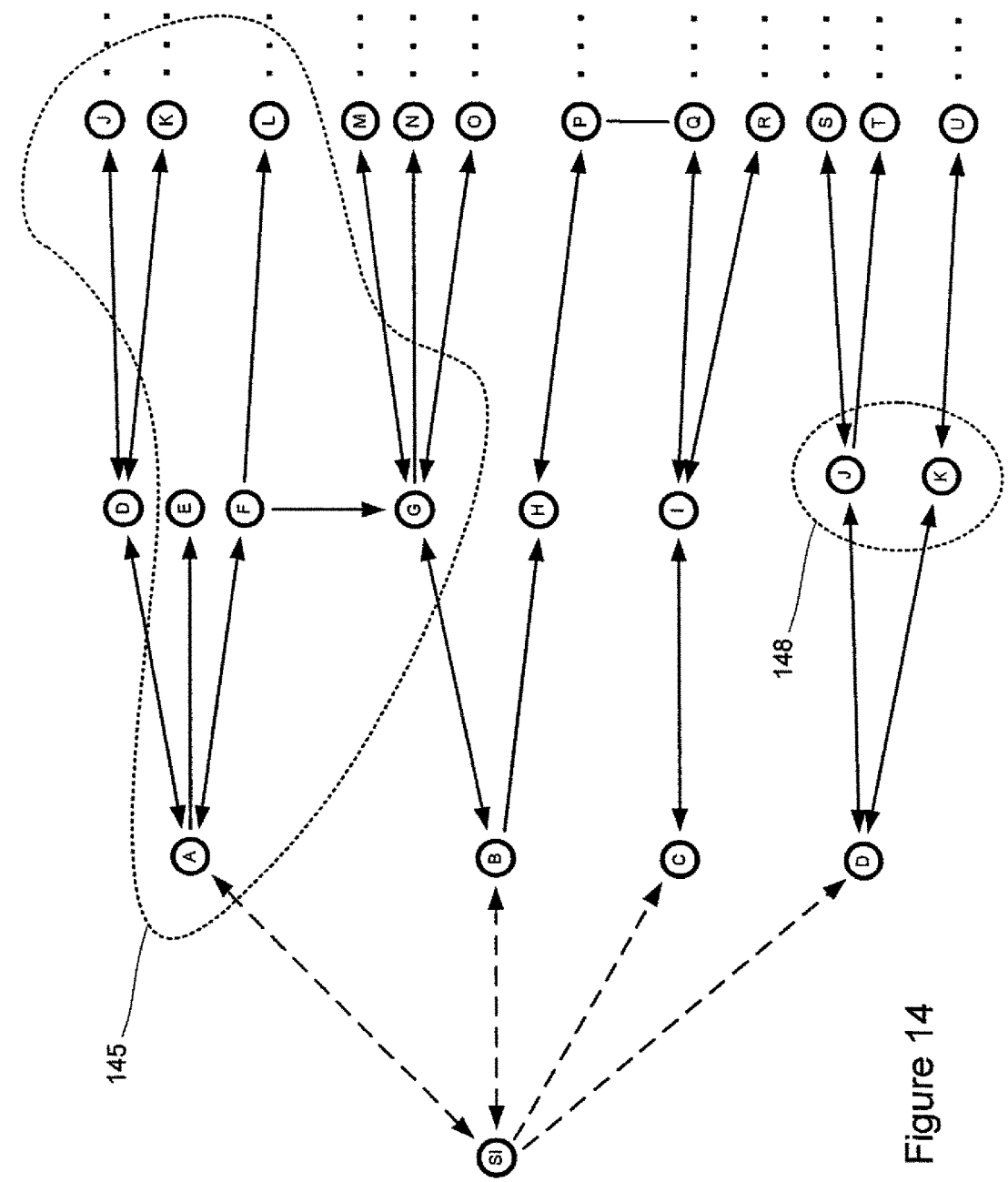
FIG. 14 is a schematic illustration of a PCN of a search initiator, wherein a portion of the PCN including databases that are eligible to be displayed as results of a directed search is identified.

Also in FIG. 14, it should be noted that physicians S, T and U are not included in the eligible portion of the search initiator's PCN, even though those physicians are separated from the search initiator by three degrees of separation down the branch beginning with physician D and are indirectly linked to physician D, who can act as an intervening database in this example. This is so because physician D is a first-degree contact of the search initiator and was not selected as an anchor database. Thus, the directed search cannot proceed in this example down the branch beginning with physician D because physician D is a non-selected first-degree contact. Instead, the directed search of this example must proceed down the branch beginning with physician A as the selected anchor database. The degrees of separation from the search initiator in this example must be determined according to the relationships as they exist within the branch beginning with a selected anchor database. Not selecting physician D as an anchor database prevents databases in that branch of the search initiator's PCN from being included among social-network members who are eligible to be displayed as directed search results, unless the databases in physician D's branch are indirectly linked to the search initiator within the branch beginning with the anchor database and are within the maximum allowable degrees of separation relative to the search initiator in that branch. According to the present example, physicians S, T and U would be included in the portion of the search initiator's PCN that is eligible to be displayed as search results if the maximum allowable degrees of separation relative to the search initiator is set greater than or equal to 4. This is true since physician A is specified as the anchor database and the separation of a database during a directed search must be determined according to that database's position in the branch of the search initiator's PCN beginning with the anchor database. Thus, when tracing a chain of communication from the search initiator to any search result, the first intervening database between the search initiator and any further removed databases must be the anchor database. Therefore, physicians S, T and U in this example are considered to be separated from the search initiator by four degrees of separation looking down the branch of the search initiator's PCN beginning with the anchor database instead of by three degrees of separation looking down the branch of the search initiator's PCN beginning with physician D.

Yet another example may include computer-executable instructions that will limit the search results returned by a directed search and to be displayed to the search initiator to the search results that are linked to the search initiator by the shortest communication path that includes the anchor database(s). Again, consider the personal communication network of the search initiator shown in FIG. 14. The maximum allowable degrees of separation between the search initiator and displayable directed search results is set to 3, as indicated by the dashed line 145, physician A is selected as an anchor database and physician D is not. Further suppose that physician J is likely to possess information about the search string and satisfies any other search criteria for a particular directed search. The computer-executable instructions cause physician J to be excluded from the displayable search results because the shortest communication path between the search initiator and physician J is through the direct link between the search initiator and physician D, as enclosed by dashed line 148. The shortest communication path is from the search initiator to physician D and then to physician J, and not from the search initiator, to physician A, to physician D, and then to physician J as shown within dashed line 145. In other words, the number of intervening contacts between physician J and the search initiator by starting at the anchor database (physician A) is not the shortest available, and thus, physician J would not be displayed as a search result returned by the directed search.

The search results of the directed search to be displayed to the search initiator can also be ordered similar to the search results returned by the broadcast search, as shown in FIG. 15. FIG. 15 is an illustrative display of search results returned by the directed search executed with Ann K. Smith, Seto L. Craig and David K. Brown as the anchor databases, as shown in FIG. 9. The search results are grouped according to the number of degrees separating each search result from the search initiator. For example, the search string that returned the search results shown in FIG. 15 was "piriformis syndrome," which is listed in the search-string field 95. The first-degree, or direct contacts of this particular search initiator (which is Mike Markus, as shown in the upper right corner of FIG. 15) that are likely to possess information pertaining to piriformis syndrome include those in the highlighted region 152 in the first column 155, which is labeled "1st Degree (Your Colleagues)." Likewise, those members of the search initiator's PCN who are separated from the search initiator by two degrees of separation and are likely to possess information on piriformis syndrome are located in the highlighted region 158 of the second column 162, labeled "2nd Degree (Your Colleagues' Colleagues)." These second-degree contacts are located adjacent to first-degree contacts in a non-highlighted region 165 of the first column 155. The first-degree contacts in this non-highlighted region 165 of the first column 155 are intervening contacts, also referred to as intervening nodes, disposed between the search initiator and the second-degree contacts in the region 158 who were displayed as search results of the directed search.

This method of returning search results can continue out to the desired maximum number of degrees of separation to be displayed as search results that was specified by the search initiator, or to the default value in the absence of a search-initiator defined value. Thus, third-degree contacts in the highlighted region 168 of the third column 172 labeled "$3^{rd}$ Degree (And Beyond)" are separated from the search initiator by two intervening contacts, which are first and second degree contacts of the search initiator located in the non-highlighted region 124 of the first and second columns 155, 162, respectively.

As can be seen from FIG. 15, only those first-degree contacts selected as an anchor database by the search initiator can be listed in the $1^{st}$-degree contact column 155 as intervening contacts between the search initiator and various search results for a directed search. This is contrasted with the many different first-degree contacts listed in the $1^{st}$-degree contact column 109 of FIG. 8, which displays the search results of a broadcast search.

Although the description of databases above makes reference to a social network of physicians, the technology is equally viable for any type of social network, where the databases can be people, professionals, corporate entities, partnerships, the like.

Example systems and methods can optionally utilize historical data regarding at least one of search activity and activity relating to the invitation and acceptance method discussed above in identifying social-network members that are more likely to posses desired information than other social-network members. In most instances, more than one search result will be returned by a search, whether broadcast or directed. The historical data can be used to identify which of the search results returned by a search of the social network, the search initiator's PCN, or both that is most likely to posses the sought after information. However, other examples can utilize the historical data apart from the search string and any other search criteria to identify a database within the social network, the search initiator's PCN, or both that is most likely to posses the sought after information.

Each time a directed search is performed, an electronic record can be established by recording on a computer-accessible medium the identity of the search initiator, each anchor database selected by the search initiator, and the search string. Similar to a communication link, each entry recorded on the computer-accessible medium establishes what is referred to herein as an inferential link. Just as with the communication link, an inferential link as used herein represents an electronic record of an inference on the part of a search initiator in conducting a directed search for information related to a search string, that the one or more anchor database(s) selected is believed by the search initiator to possess information related to the search string. The existence of an inferential link pointing to a particular database about a topic serves as a weighting factor that supports an inference that the particular database is more likely to possess useful information about the topic than other databases to which no, or fewer inferential links point.

Figure 16:
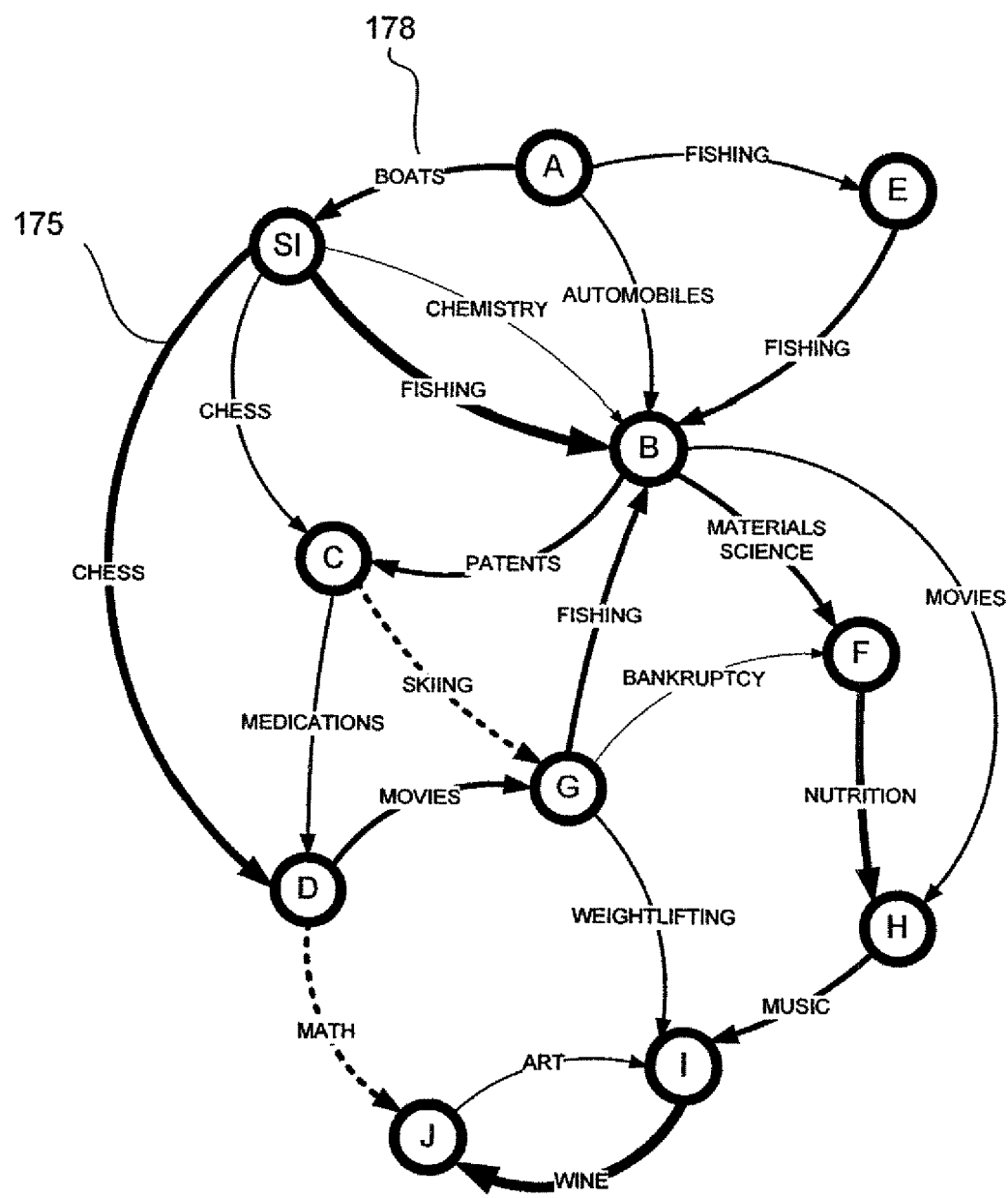
FIG. 16 is an illustrative arrangement of a network of databases (the search initiator and physicians A-J) linked together by inferential links.

FIG. 16 is an illustrative arrangement of a network of databases (the search initiator and physicians A-J) linked together by inferential links 175. The network of databases in FIG. 16 can optionally be generated according to computer-readable instructions to provide an observer with a graphical depiction of the perceived flow of information. Each inferential link may also be provided with a topic 178 that identifies a topic related to a search string entered by the search initiator in conducting a directed search.

Consider, for example, the inferential link 175 extending between the search initiator and physician B. The directionality of the inferential link 175 (indicated by the direction of the arrow head points) points away from the search initiator and towards physician B, indicating that the search initiator previously executed a directed search for information related to "fishing" with physician B as the anchor database.

The relative strength of each inferential link 175 relative to other inferential links can vary over time. The relative strength of each inferential link 175 in FIG. 16 is illustrated by the weight of the line connecting the respective databases The inferential link in the context of fishing between the search initiator and physician B is stronger than the inferential link 175 about chess between the search initiator and physician C, as indicated by the relative line weights. The relative strength of inferential links can vary over time, and can be influenced by any number of factors that are indicative of the likelihood that a database is a useful source of information about a given topic. For instance, repeating a directed search for information about the same, or a related topic increases the strength of an inferential link relative to an inferential link established by conducting a single directed search. Similarly, the higher the frequency with which the same or a related directed search is performed increases the strength of an inferential link relative to inferential links established by directed searches conducted at a lower frequency.

The relative strength of each inferential link can also be decayed over time. Periods of time during which the same or a related directed search is not performed can support the inference that the anchor database previously selected by the search initiator is no longer a useful source of information about a topic. Accordingly, the strength of the inferential link between the search initiator and the anchor database is weakened relative to its strength following the previous directed search as a function of time. And after a suitable period of time has lapsed without any further directed search activity, the electronic record forming the inferential link can optionally be deleted, or otherwise removed from consideration in determining the database that is most likely to possess useful information about a topic.

The strength of the inferential link is the weight afforded to the historical data in ordering the search results to be displayed to the search initiator. The stronger the inferential link, the more weight will be given to the electronic data recorded on the computer-readable medium represented by the inferential link in determining which database is most likely to possess useful information about a topic defined by the search string.

Another method for utilizing historical data represented by inferential links to identify the database that is most likely to possess the useful information is to follow the perceived flow of information. Databases having a plurality of inferential links with a directionality pointing towards them with regard to a topic are considered more likely to possess useful information about that topic than databases with no, or only a single inferential link pointing towards them. For example, there are three inferential links 175 pointing toward physician B in the context of fishing. Thus, at least three social-network members have specified physician B as an anchor database in conducting a search for information related to fishing. The topic of fishing can be a category under which a plurality of subcategories related to fishing exist, it can be the actual search string, or any other topic identifier.

Further, the inferential-link historical data can rank databases based on their likelihood to possess useful information based on the relationships between the databases themselves. For example, in determining which of physicians A, B and E is most likely to posses information about fishing, it can be observed that physician A has previously conducted a directed search for such information specifying physician E as the anchor database, Thus, it is inferred, that physician E is more likely than physician A to possess useful information about fishing. Similarly, physician E has previously conducted a directed search for fishing naming physician B as the anchor database. Accordingly, the computer-readable logic of the present invention can determine that physician B is more likely than physician E to possess useful information about fishing. Additionally, the number of inferential links in the context of fishing that point toward physician B can also be factored into the determination of physician B as the most likely of those physicians pictured in FIG. 16 to possess useful information about fishing.

This written description uses examples to disclose the invention, including the best mode, and also to enable a person skilled in the art to make and use the invention. The patentable scope of the invention may include other examples that occur to those skilled in the art.

It is further noted that the systems and methods described herein may be implemented on various types of computer architectures, such as for example on a single general purpose computer or workstation, or on a networked system, or in a client-server configuration, or in an application service provider configuration.

It is further noted that the systems and methods may include data signals conveyed via networks (e.g., local area network, wide area network, internet, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The systems' and methods' data (e.g., associations, mappings, etc.) may be stored and implemented in one or more different types of computer-implemented ways, such as different types of storage devices and programming constructs (e.g., data stores, RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

What is claimed is:

1. A method for conducting a search of a social network, said method comprising:

receiving by at least one processor a social network comprised of nodes interconnected by links, the nodes corresponding to members of the social network, and the links connecting corresponding pairs of nodes;

receiving by at least one processor a search term or phrase from a search initiator, the search initiator being a member of the social network;

receiving historical data identifying one or more nodes of the social network that are directly linked to a historical node and that the corresponding member of the historical node determined to have data relevant to the search term or phrase;

generating inferential links to identify one or more relevant databases based on the historical data for the search term or phrase;

performing the search using the one or more relevant databases, wherein the searching includes:

searching nodes of the social network directly linked to the historical node, wherein the directly searched nodes include only the nodes of the social network identified in the historical data; and searching nodes of the social network indirectly linked to the historical node, wherein the indirectly searched nodes include only nodes of the social network linked to the nodes of the social network identified in the historical data; and returning by at least one processor the search results and a set of instructions describing how the search results are to be displayed to the search initiator, the set of instructions instructing that the search results are to be displayed by showing how a node corresponding to one of the search results is linked to a node corresponding to the search initiator in the social network;

wherein the set of instructions instruct that the search results are to be displayed by:

showing a path between the node corresponding to the one of the search results and the node corresponding to the search initiator by visually representing links of the path as straight lines and nodes of the path as dots or circles.

2. The method according to claim 1, wherein the links include corresponding contexts in which the members consult with each other, and wherein said method further includes:
receiving a search context from the search initiator, wherein the search context is one of the corresponding contexts, and wherein the searching is limited to members of the social network connected to the search initiator node by links with corresponding contexts being the search context.

3. The method according to claim 2, wherein the searching is limited to members of the social network connected to the search initiator by paths formed of only links with corresponding contexts being the search context.

4. The method according to claim 2, wherein the corresponding contexts represent areas of specialization.

5. The method according to claim 1, wherein the nodes includes databases of data regarding the corresponding members of the social network, and wherein the searching includes searching the databases for the search term or phrase.

6. The method according to claim 1, further including:
identifying an additional search term or phrase associated with the search term or phrase;
searching the social network for the additional search term or phrase to generate additional search results, the additional search results corresponding to the nodes of the social network; and
returning the additional search results with the search results, wherein the set of instructions instruct that the additional search results are to be displayed with the search results.

7. The method according to claim 1, further including:
determining an ordering of the search results by a mathematical algorithm ranking the search results based on one or more of: similarity to the search initiator; and physical proximity to the search initiator;
wherein the set of instructions instruct that the search results are to be displayed in the determined order.

8. The method according to claim 1, wherein the links indicate unidirectional directions of trust between the corresponding pairs of nodes, and wherein the searching traverses the social network along the links only in the directions of trust starting from the node corresponding to the search initiator.

9. The method according to claim 8, further including:
receiving local data identifying one or more nodes of the social network that are directly linked to the node corresponding to the search initiator and that the search initiator determines to have data relevant to the search term or phrase, wherein the searching further includes:
searching nodes of the social network directly linked to the node corresponding to the search initiator, wherein the directly searched nodes include only the one or more nodes of the social network identified in the local data; and
searching nodes of the social network indirectly linked to the node corresponding to the search initiator, wherein the indirectly searched nodes include only nodes of the social network linked to the one or more nodes of the social network identified in the local data.

10. The method according to claim 9, wherein the local data identifies only one node of the social network that is directly linked to the node corresponding to the search initiator and that the search initiator determines to have data relevant to the search term or phrase.

11. The method according to claim 1, wherein the historical data is derived from prior searches of the social network performed by the corresponding member of the historical node.

12. The method according to claim 1, wherein the historical data includes local data from prior searches of the social network performed by the corresponding member of the historical node, the local data identifying one or more nodes of the social network that are directly linked to the historical node and that the corresponding member of the historical node determines to have data relevant to the search term or phrase.

13. A system for conducting a search of a social network, said system comprising:
at least one processor configured to:
receive the social network comprised of nodes interconnected by links, the nodes corresponding to members of the social network, and the links connecting corresponding pairs of nodes;
receive a search term or phrase from a search initiator, the search initiator being one of the members of the social network;
receive historical data identifying one or more nodes of the social network that are directly linked to a historical node and that the corresponding member of the historical node determined to have data relevant to the search term or phrase;
generate inferential links to identify one or more relevant databases based on the historical data for the search term or phrase;
perform the search using the one or more relevant databases, wherein the searching includes:
searching nodes of the social network directly linked to the historical node, wherein the directly searched nodes include only the nodes of the social network identified in the historical data; and
searching nodes of the social network indirectly linked to the historical node, wherein the indirectly searched nodes include only nodes of the social network linked to the nodes of the social network identified in the historical data;
return the search results and a set of instructions describing how the search results are to be displayed to the search initiator, the set of instructions instructing that the search results are to be displayed by showing how a node corresponding to one of the search results is linked to a node corresponding to the search initiator in the social network; and
determine an ordering of the search results by a mathematical algorithm ranking the search results based on one or more of: similarity to the search initiator; and physical proximity to the search initiator;
wherein the set of instructions instruct that the search results are to be displayed in the determined order.

14. The system according to claim 13, wherein the nodes includes databases of data regarding the corresponding members of the social network, and wherein the searching includes searching the databases for the search term or phrase.

15. The system according to claim 13, wherein the at least one processor is further configured to:
identify an additional search term or phrase associated with the search term or phrase;
search the social network for the additional search term or phrase to generate additional search results, the additional search results corresponding to the nodes of the social network; and return the additional search results with the search results, wherein the set of instructions instruct that the additional search results are to be displayed with the search results.

16. The system according to claim 13, wherein the links indicate directions of trust between the corresponding pairs of nodes, and wherein the searching traverses the social network along the links only in the directions of trust starting from the node corresponding to the search initiator.

17. The system according to claim 16, wherein the at least one processor is further configured to:
   receive local data identifying one or more nodes of the social network that are directly linked to the node corresponding to the search initiator and that the search initiator determines to have data relevant to the search term or phrase, wherein the searching further includes:
   searching nodes of the social network directly linked to the node corresponding to the search initiator, wherein the directly searched nodes include only the one or more nodes of the social network identified in the local data; and
   searching nodes of the social network indirectly linked to the node corresponding to the search initiator, wherein the indirectly searched nodes include only nodes of the social network linked to the one or more nodes of the social network identified in the local data.

* * * * *